United States Patent [19]

Caskey et al.

[11] Patent Number: 5,364,759

[45] Date of Patent: Nov. 15, 1994

[54] DNA TYPING WITH SHORT TANDEM REPEAT POLYMORPHISMS AND IDENTIFICATION OF POLYMORPHIC SHORT TANDEM REPEATS

[75] Inventors: Charles T. Caskey; Albert O. Edwards, both of Houston, Tex.

[73] Assignee: Baylor College of Medicine, Houston, Tex.

[21] Appl. No.: 647,655

[22] Filed: Jan. 31, 1991

[51] Int. Cl.$^5$ .................. C12Q 1/68; C07H 15/12; G01N 33/48; G01N 33/566
[52] U.S. Cl. ........................................ 435/6; 436/94; 536/24.31; 935/77; 935/78
[58] Field of Search .............. 435/6, 91; 436/94; 935/77, 78; 536/27, 24.3, 24.31, 24.33, 25.32

[56] References Cited

FOREIGN PATENT DOCUMENTS

| | | |
|---|---|---|
| 0266787 | 5/1988 | European Pat. Off. . |
| 0298656 | 1/1989 | European Pat. Off. . |
| 0337625 | 10/1989 | European Pat. Off. . |
| 2166445 | 8/1986 | United Kingdom . |

OTHER PUBLICATIONS

Savatier, et al; Evolution of the Primate β-Globin Gene Region. High Rate of Variation in CpG Dinucleotides and in Short Repeated Sequences between Man and Chimpanzee; J. Mol. Biol. 182:21–29 (1985).
Boylan, et al; Repetitive DNA (TGGA)$_n$ 5′ to the Human Myelin Basic Protein Gene: A New Form of Oligonucleotide Repetitive Sequence Showing Length Polymorphism; Genomics 6:16–22 (1990).
Semenza, et al; Detection of a Novel DNA Polymorphism in the β-Globin Gene Cluster; The Journal of Biological Chemistry, 259:6045–6048 (1984).
Chebloune, et al; Structural analysis of the 5′ flanking region of the β-globin gene in African sickle cell anemia patients: Further evidence for three origins of the sickle cell mutation in Africa; Proc. Natl. Acad. Sci. USA, 85:4431–4435 (1988).
Love, et al; Towards construction of a high resolution map of the mouse genome using PCR–analysed microsatellites; Nucleic Acids Res., 18:4123–4130 (1990).
Zuliani, et al: A High Frequency of Length Polymorphisms in Repeated Sequences Adjacent to Alu Sequences; Am. J. Hum. Genet. 46:963–969 (1990).
Sinnett, et al; Alumorphs–Human DNA Polymorphisms Detected by Polymerase Chain Reaction Using *Alu*-Specific Primers; Genomics, 7:331–334 (1990).
Turner, et al; Genetic variation in clonal vertebrates (List continued on next page.)

*Primary Examiner*—Robert A. Wax
*Assistant Examiner*—Dian C. Jacobson
*Attorney, Agent, or Firm*—Fulbright & Jaworski

[57] ABSTRACT

The present invention relates to a DNA profiling assay for detecting polymorphisms in a short tandem repeat. The method includes the steps of extracting DNA from a sample to be tested, amplifying the extracted DNA and identifying the amplified extension products for each different sequence. Each different sequence is differentially labeled. In the method, internal and external standards can also be used. The method is applicable to a wide variety of forensic and medical samples, including blood, semen, vaginal swaps, tissue, hair, saliva, urine and mixtures of body fluids. A short tandem repeat sequence which can be characterized by the formula $(A_wG_xT_yC_z)_n$, wherein A, G, T and C represent the nucleotides, w, x, y and z represent the number of nucleotide and range from 0 to 7 and the sum of w+x+y+z ranges from 3 to 7 and n represents the repeat number and ranges from 5 to 50. The labels can be from a variety of groups, including fluorescers, radioisotopes, chemiluminescers, stains, enzymes and antibodies. Also described is a kit. Further, a method of detecting the polymorphic short tandem repeats comprising the steps of either searching for the repeats in a data base or comparing oligonucleotides and searching for the repeats in a genetic library.

25 Claims, 13 Drawing Sheets

OTHER PUBLICATIONS detected by simple-sequence DNA fingerprinting; Proc. Natl. Acad. Sci., 87:5653–5657 (1990).

Beroldingen, et al; Applications of PCR to the Analysis of Biological Evidence; PCR Technology, H. Erlich, Ed., Stockton Press, N.Y., 209–223 (1989).

Weber, J. L.; Length Polymorphisms in (dC-dA)$_n$·(dG-dT)$_n$ Sequences Detected Using the Polymerase Chain Reaction; Polymerase Chain Reaction, H. A. Erlich, R. Gibbs, H. H. Kazazian, Jr., Eds.; Cold Spring Harbor Laboratory Press, 141–146 (1989).

Landegren, et al; A Ligase-Mediated Gene Detection Technique; Science, 241:1077–1080 (1988).

Devlin, et al; No Excess of Homozygosity at Loci Used for DNA Fingerprinting; Science, 249:1416–1420 (1990).

Boerwinkle, et al; Rapid typing of tandemly repeated hypervariable loci by the polymerase chain reaction: Application to the apolipoprotein B 3' hypervariable region; Proc. Natl. Acad. Sci., 86:212–216 (1989).

Litt, et al; A Hypervariable Microsatellite Revealed by In Vitro Amplification of a Dinucleotide Repeat within the Cardiac Muscle Actin Gene; Am. J. Hum. Genet., 44:397–401 (1989).

Weber, et al; Abundant Class of Human DNA Polymorphisms Which Can Be Typed Using the Polymerase Chain Reaction; Am. J. Hum. Genet., 44:388–396 (1989).

Weber, James L.; Informativeness of Human (dC-dA)$_n$·(dG-dT)$_n$ Polymorphisms; Genomics, 7:524–530 (1990).

Jeffreys, et al; Repeat Unit Sequence Variation in Minisatellites: A Novel Source of DNA Polymorphism for Studying Variation and Mutation by Single Molecule Analysis; Cell, 60:473–485 (1990).

Müller, et al; A finger printing by oligonucleotide probes specific for simple repeats; Human Genetics, 74:239–243 (1986).

Jeffreys, et al; Individual-specific 'fingerprints' of human DNA; Nature, 316:76–79 (1985).

Ali, et al; Intrinsic polymorphism of variable number tandem repeat loci in the human gene; Nucleic Acids Research, vol. 16, No. 17 (1988).

Odelberg, et al; Characterization of Eight VNTR Loci by Agarose Gel Electrophoresis; Genomics, 5:915–924 (1989).

Smeets, et al; Use of variable simple sequence motifs as genetic markers: application to study of myotonic dystrophy; Human Genetics 83:245–251 (1989).

Nakamura, et al; Variable Number of Tandem Repeat (VNTR) Markers for Human Gene Mapping; Science, 235:1616–1622 (1987).

Orita, et al; Rapid and Sensitive Detection of Point Mutations and DNA Polymorphisms Using the Polymerase Chain Reaction; Genomics, 5:874–879 (1989).

Jeffreys, et al; Amplification of human minisatellites by the polymerase chain reaction; towards DNA fingerprinting of single cells; Nucleic Acids Research, 16:10953–10971 (1988).

Epstein, et al; The 3' ends of *alu* repeats are highly polymorphic; Nucleic Acids Research, 18:4634 (1990).

Tautz, et al; Cryptic simplicity in DNA is a major source of genetic variation; Nature 322:652–656 (1986).

Riley, et al; A novel, rapid method for the isolation of terminal sequences from yeast artificial chromosome (YAC) clones; Nucleic Acids Research, 18:2887–2890 (1990).

Tautz, et al; Simple sequences are ubiquitous repetitive compounds of eukaryotic genomes; Nucleic Acids Research, 12:4127–4138 (1984).

Nanda, et al; Heterogeneities in the distribution of (GACA)$_n$ simple repeats in the karyotypes of primates and mouse; Human Genetics, 85:187–194 (1990).

Nürnberg, et al; DNA Fingerprinting with the oligonu- (List continued on next page.)

OTHER PUBLICATIONS cleotide probe (CAC)$_5$/GTG)$_5$: somatic stability and germline mutations; Human Genetics, 84:75–78 (1989).

Economou, et al; The polydeoxyadenylate tract of *Alu* repetitive elements is polymorphic in the human genome; Proc. Natl. Acad. Sci., 87:2951–2954 (1990).

Dryia, et al; Parental origin of mutations of the retinoblastoma gene; Nature, 339:556–558 (1989).

Ploos, et al; Tetranucleotide repeat polymorphism in the vWF gene; Nucleic Acids Research, 18:4957.

Zuliani, et al; Tetranucleotide repeat polymorphism in the apolipoprotein B gene; Nucleic Acids Research, 18:4299.

Zuliani, et al; Tetranucleotide repeat polymorphism in the apolipoprotein C–III gene; Nucleic Acids Research, 18:4299.

Zuliani, et al; Tetranucleotide repeat polymorphism in the LPL gene; Nucleic Acids Research, 18:4958.

Lagoda, et al; Increased detectability of somatic changes in the DNA from human tumours after probing with "synthetic" and "genome-derived" hypervariable multilocus probes; Human Genetics, 84:35–40 (1989).

Tautz, Diethard; Hypervariability of simple sequences as a general source for polymorphic DNA markers; Nucleic Acids Research, 17:6463–6471 (1989).

Roberts, et al; Detection of novel genetic markers by mismatch analysis; Nucleic Acids Research, 17:5961–5971 (1989).

Gibbs, et al; Multiplex DNA Deletion Detection and Exon Sequencing of the Hypoxanthine Phosphoribosyltransferase Gene in Lesch–Nyhan Families; Genomics, 7:235–244 (1990).

Edwards, et al; Automated DNA Sequencing Methods for Detection and Analysis of Mutations; Applications to the Lesch–Nyhan Syndrome; Reprinted from the Transactions of the Association of American Physicians vol. CII:185–194 (1989).

HUMHPRTB[AGAT]$_n$ and HUMFABP[AAT]$_n$

HUMRENA4[ACAG]$_n$
and
HUMTH01[AATG]$_n$

100

SEQUENCE LISTING ( 1 ) GENERAL INFORMATION:

( i i i ) NUMBER OF SEQUENCES: 26

( 2 ) INFORMATION FOR SEQ ID NO: 1:

( i ) SEQUENCE CHARACTERISTICS:
        ( A ) LENGTH: 52
        ( B ) TYPE: Nucleic Acid
        ( C ) STRANDEDNESS: Single
        ( D ) TOPOLOGY: Linear ( i i ) MOLECULE TYPE: Synthetic DNA ( x i ) SEQUENCE DESCRIPTION: SEQ ID NO: 1:

```
ACTGCAGAGA    CGCTGTCTGT    CGAAGGTAAG                40

GAACGGACGA    GAGAAGGGAG    AG                        52
```

( 2 ) INFORMATION FOR SEQ ID NO: 2:

( i ) SEQUENCE CHARACTERISTICS:
        ( A ) LENGTH: 52
        ( B ) TYPE: Nucleic Acid
        ( C ) STRANDEDNESS: Single
        ( D ) TOPOLOGY: Linear ( i i ) MOLECULE TYPE: Synthetic DNA ( x i ) SEQUENCE DESCRIPTION: SEQ ID NO: 2:

```
        CTCTCCCTTC   TCGAATCGTA   ACCGTTCGTA                    40

CGAGAATCGC   TGTCTCTGCA   GT                       52
```

( 2 ) INFORMATION FOR SEQ ID NO: 3:

( i ) SEQUENCE CHARACTERISTICS:
        ( A ) LENGTH: 38
        ( B ) TYPE: Nucleic Acid
        ( C ) STRANDEDNESS: Single
        ( D ) TOPOLOGY: Linear ( i i ) MOLECULE TYPE: Synthetic DNA ( x i ) SEQUENCE DESCRIPTION: SEQ ID NO: 3:

```
        GCCGGATCCC   GAATCGTAAC   CGTTCGTACG                    30

AGAATCGC                   38
```

( 2 ) INFORMATION FOR SEQ ID NO: 4:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Synthetic DNA ( x i ) SEQUENCE DESCRIPTION: SEQ ID NO: 4:

```
        TACGAGAATC   GCTGTCTCTG   CAGT                     24
```

( 2 ) INFORMATION FOR SEQ ID NO: 5:

( i ) SEQUENCE CHARACTERISTICS:
        ( A ) LENGTH: 25
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 5:

```
        GTAGTATCAG   TTTCATAGGG   TCACC                    25
```

( 2 ) INFORMATION FOR SEQ ID NO: 6:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 6:

```
        CAGTTCGTTT   CCATTGTCTG   TCCG                     24
```

( 2 ) INFORMATION FOR SEQ ID NO: 7:

( i ) SEQUENCE CHARACTERISTICS:
    ( A ) LENGTH: 24
    ( B ) TYPE: Nucleic Acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 7:

TCCAGAATCT    GTTCCAGAGC    GTGC    24

( 2 ) INFORMATION FOR SEQ ID NO: 8:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 8:

GCTGTGAAGG    TTGCTGTTCC    TCAT    24

( 2 ) INFORMATION FOR SEQ ID NO: 9:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 9:

TGTGAGTCCC    AGTTGCCAGT    CTAC    24

( 2 ) INFORMATION FOR SEQ ID NO: 10:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 10:

ACTGGTCACC    TTGGAAAGTG    GCAT    24

( 2 ) INFORMATION FOR SEQ ID NO: 11:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 11:

TGAGGGCTGT    ATGGAATACG    TTCA    24

( 2 ) INFORMATION FOR SEQ ID NO: 12:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 12:

CAAGCACCAA    GCTGAGCAAA    CAGA    24

( 2 ) INFORMATION FOR SEQ ID NO: 13:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 13:

GTGGGCTGAA    AAGCTCCCGAT    TAT    23

( 2 ) INFORMATION FOR SEQ ID NO: 14:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 14:

ATTCAAAGGG    TATCTGGGCT    CTGG    24

( 2 ) INFORMATION FOR SEQ ID NO: 15:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 15:

GGAGAGACAG    GATGTCTGGC    ACAT    24

( 2 ) INFORMATION FOR SEQ ID NO: 16:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 16:

CCATCTCTCT    CCTTAGCTGT    CATA    24

( 2 ) INFORMATION FOR SEQ ID NO: 17:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 17:

AGAGTACCTT    CCCTCCTCTA    CTCA    24

( 2 ) INFORMATION FOR SEQ ID NO: 18:

( i ) SEQUENCE CHARACTERISTICS:
    ( A ) LENGTH: 24
    ( B ) TYPE: Nucleic Acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 18:

CTCTATGGAG CTGGTAGAAC CTGA    24

( 2 ) INFORMATION FOR SEQ ID NO: 19:

( i ) SEQUENCE CHARACTERISTICS:
    ( A ) LENGTH: 24
    ( B ) TYPE: Nucleic Acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 19:

ATGCCACAGA TAATACACAT CCCC    24

( 2 ) INFORMATION FOR SEQ ID NO: 20:

( i ) SEQUENCE CHARACTERISTICS:
    ( A ) LENGTH: 24
    ( B ) TYPE: Nucleic Acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 20:

CTCTCCAGAA TAGTTAGATG TAGG    24

( 2 ) INFORMATION FOR SEQ ID NO: 21:

( i ) SEQUENCE CHARACTERISTICS:
    ( A ) LENGTH: 24
    ( B ) TYPE: Nucleic Acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 21:

CTCCTTGTGG CCTTCCTTAA ATGG    24

( 2 ) INFORMATION FOR SEQ ID NO: 22:

( i ) SEQUENCE CHARACTERISTICS:
    ( A ) LENGTH: 24
    ( B ) TYPE: Nucleic Acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 22:

CTTCTCCAGC ACCCAAGGAA GTCA    24

( 2 ) INFORMATION FOR SEQ ID NO: 23:

( i ) SEQUENCE CHARACTERISTICS:
    ( A ) LENGTH: 32
    ( B ) TYPE: Nucleic Acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 23:

```
TTACGCGTAT  TCAAAGGGTA  TCTGGGCTCT  GG                32
```

( 2 ) INFORMATION FOR SEQ ID NO: 24:

( i ) SEQUENCE CHARACTERISTICS:
        ( A ) LENGTH: 32
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 24:

```
TTACGCGTCT  CGGACAGTAT  TCAGTTCGTT  TC                32
```

( 2 ) INFORMATION FOR SEQ ID NO: 25:

( i ) SEQUENCE CHARACTERISTICS:
        ( A ) LENGTH: 34
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 25:

```
TTACGCGTTC  TCCAGAATAG  TTAGATGTAG  GTAT              34
```

( 2 ) INFORMATION FOR SEQ ID NO: 26:

( i ) SEQUENCE CHARACTERISTICS:
        ( A ) LENGTH: 504
        ( B ) TYPE: Nucleic Acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 27:

```
TGTTTGTTTT  GTTTGTTGT   TTTTTTTAAA  TCTGTTCTCA   40
TTGGTGTTTC  TGTTTGCTGC  CTTCTCCAGC  ACCCAAGGAA   80
GTCACCACCA  TATTGTTCCT  TAGTCCTGTG  TTTCTTAGCT  120
GGTCTGCCTT  CTTCTCTCCA  CTTTTCAGAG  TCAGATAGAT  160
GATAGATAGA  TAGATAGATA  GATAGATAGA  TAGATAGATA  200
GATATAAAAA  GATAAATAGA  TAGTCTCTAT  ACAGATATAG  240
ATGTATATCA  TTCCAAGTTT  TAGCTGTATT  TGCAGGAGGA  280
AACGAGAAGT  ATGTCTACTT  CTTTTCCTCT  GGAACCAGAG  320
GTTTCCCCTT  TGTTACCTTG  TTTTTCCATT  TAAGGAAGGC  360
CACAAGGAGA  ACCATGAATC  TGCTCTAATT  GATTTTACG   400
AAAGGAAGGA  GAAAAGACA   GGAAATAATT  CACAATCTCC  440
AACTCTTTCA  TCGTAATTAG  TGAGTGACAA  GTAGTTTGTA  480
ACACTCTCAG  TGTATCTTGA  TAAT                    504
```

DNA TYPING WITH SHORT TANDEM REPEAT POLYMORPHISMS AND IDENTIFICATION OF POLYMORPHIC SHORT TANDEM REPEATS

FIELD OF THE INVENTION

The present invention relates generally to a method of DNA typing for the detection of short tandem repeat sequence polymorphisms. More particularly, it relates to the method of detecting short tandem repeat sequences which show polymorphisms in the number of repeats for the detection or identification of medical and forensic samples, paternity, sample origin and tissue origin. Additionally it further relates to the method of identifying polymorphic short tandem repeats in genomes.

BACKGROUND OF THE INVENTION

The volume of crime committed in the United States has risen with the increase of population and expansion of population centers. A large portion of violent crimes involve the creation of body fluid evidence having the potential of providing significant information about the perpetrator of a particular offense. Although the forensic science community has made tremendous effort in using this evidence, the results have historically been limited and are not useful in many situations when dealing with human remains and crime scene evidence. Identification by genetically inherited markers has long been seen as a possibility that would overcome most of the problems that are encountered when identification is not accomplished by fingerprints, forensic odontology, medical records or other methods. The establishment of a genetically inherited method that could be used for identification would have tremendous impact on investigation of the violent crimes of sexual assault and murder, identification of human remains and missing persons, and disputed parentage.

Methods enabling the matching of unidentified tissue samples to specific individuals would have wide application in the criminal justice system and the forensic sciences. With the possible exception of monozygotic twins, each individual in the human population has a unique genetic composition which could be used to specifically identify each individual. This phenomenon presents the theoretical possibility of using DNA sequence variation to determine whether a forensic sample was derived from any given individual.

Genetic marker systems, including blood groups and isoenzymes, have been used by forensic and medical serologists to provide estimates of individuality ranging from 1:1000 to 1:1,000,000 using 10 to 15 markers. Numbers in this range are often not available since a large percentage of the evidence does not yield results for ten genetic marker systems. Forensic scientists, investigators and the court system have been using inclusions as low as 1:5 to 1:100 in a population to bolster their case against defendants.

The fields of forensic and medical serology, paternity testing, and tissue and sample origin has been altered by the use of DNA sequence variation, e.g., satellite sequences and variable number of tandem repeats (VNTRS) or AMP-FLPS, in the crime laboratory, the court, hospitals and research and testing labs. Inclusion probabilities stated by the laboratories performing the analyses in such cases often exceed 1:1,000,000. The first implementation of DNA typing in forensics, was Jeffreys' use of a multilocus DNA probe "fingerprint" that identified a suspect in a murder case occurring in England. In the United States, DNA profiling has been established using a battery of unlinked highly polymorphic single locus VNTR probes. The use of these batteries of probes permits the development of a composite DNA profile for an individual. These profiles can be compared to ethnic databases using the principles of Hardy-Weinberg to determine the probability of the match between suspect and unknown forensic samples.

The application of VNTRs to gene mapping, population genetics, and personal identification has been limited by the low frequency and asymmetric distribution of these repeats in the genome and by the inability to precisely determine alleles with Southern hybridization-based detection schemes. The inability to make precise allele determinations complicates the application of VNTRs to personal identification. Binning protocols have been devised in which all alleles occurring within a region of the gel are treated as the same allele for genotype calculations. Since the allele distribution appears continuous because of the limited resolving power of Southern gels, heterozygotes with alleles of similar size may be scored as homozygotes. These features have led to claims that VNTR loci are not in Hardy-Weinberg equilibrium, and therefore the method for calculating the significance of a match is not agreed upon.

Although these methods have markedly improved the power of the forensic and medical scientist to distinguish between individuals, they suffer from a number of shortcomings including a lack of sensitivity, the absence of internal controls, expense, time intensity, relatively large sample size, an inability to perform precise allele identification and problems with identifying degraded DNA samples.

Medical and forensic studies have also employed the polymerase chain reaction (PCR) to examine variation in the HLA locus. PCR has also been used to amplify short VNTRs or AMP-FLPs. The use of PCR addresses some of the problems of sensitivity and sample degradation, however, the HLA typing system, still has some problems. A simpler, more powerful technique is needed which makes use of the most recent advances in DNA technology.

The present invention involves the novel application of these advances to medical and forensic science. In the present invention novel classes of highly polymorphic, primarily trimeric and tetrameric, short or simple tandem repeats (STRs) which are present within the human genome have been identified. These STRs have characteristics suitable for inclusion in a DNA profiling assay. This assay incorporates internal or external standards, provides higher sensitivity, requires shorter analysis time, lowers expense, and enables precise identification of alleles. The STRs are amplified with great fidelity and the allele patterns are easily interpreted. Amplification of highly polymorphic tandemly reiterated sequences may be the most cost effective and powerful method available to the medical and forensic community.

The DNA profiling assay of the present invention has features which represent significant improvements over existing technology and brings increased power and precision to DNA profiling for criminal justice, paternity testing, and other forensic and medical uses.

SUMMARY OF THE INVENTION

An object of the present invention is a method for DNA profiling using short tandem repeat polymorphisms.

An additional object of the present invention is a method for identifying the source of DNA in a forensic or medical sample.

A further object of the present invention is to provide an automated DNA profiling assay.

An additional object of the present invention is the provision of a method for identifying and detecting short tandem repeat polymorphisms to expand the discriminating power of a DNA profiling assay.

A further object of the present invention is to extend the discriminating power of a DNA profiling assay.

An additional object of the present invention is to provide a kit for detecting short tandem repeat polymorphisms.

Thus in accomplishing the foregoing objects, there is provided in accordance with one aspect of the present invention a DNA profiling assay comprising the steps of: extracting DNA from a sample to be tested; performing multiplex polymerase chain reaction on the extracted DNA; and identifying the amplified extension products from the multiplex polymerase chain reaction for each different sequence, wherein each different sequence is differentially labelled.

The DNA profiling assay is applicable to any sample from which amplifiable DNA can be extracted. In medical and forsenic uses the samples are selected from the group consisting of blood, semen, vaginal swabs, tissue, hair, saliva, urine and mixtures of body fluids.

Specific embodiments of the invention include the use of short tandem repeat sequences selected from the group of non-duplicative nucleotide sequences consisting of:

$(AA)_m$, $(AC)_m$, $(AG)_m$, $(AT)_m$, $(CC)_m$, $(CG)_m$, $(AAC)_n$, $(AAG)_n$, $(AAT)_n$, $(ACC)_n$, $(ACG)_n$, $(ACT)_n$, $(AGC)_n$, $(AGG)_n$, $(ATC)_n$, $(CCG)_n$, $(AAAC)_n$, $(AAAG)_n$, $(AAAT)_n$, $(AACC)_n$, $(AACG)_n$, $(AACT)_n$, $(AAGG)_n$, $(AAGT)_n$, $(AATC)_n$, $(AATG)_n$, $(AATT)_n$, $(ACAG)_n$, $(ACAT)_n$, $(AGAT)_n$, $(ACCC)_n$, $(ACCG)_n$, $(ACCT)_n$, $(ACGC)_n$, $(ACGG)_n$, $(ACGT)_n$, $(ACTC)_n$, $(ACTG)_n$, $(ACTT)_n$, $(AGCC)_n$, $(AGCG)_n$, $(AGCT)_n$, $(AGGC)_n$, $(AGGG)_n$, $(ATCC)_n$, $(ATCG)_n$, $(ATGC)_n$, $(CCCG)_n$, $(CCGG)_n$ and combinations thereof wherein n and m are the repeat number and m varies from about 10 to 40 and n varies from about 5 to 40.

In another embodiment of the present invention the differential label for each specific sequence is selected from the group consisting of fluorescers, radioisotopes, chemiluminescers, enzymes, stains and antibodies. One specific embodiment uses the fluorescent compounds Texas Red, tetramethylrhodamine-5-(and-6) isothiocyanate, NBD aminoheanoic acid and fluorescein-5-isothiocyanate.

The assay can be automated by using an automated fluorescent DNA label analyzer capable of distinguishing, simultaneously, different fluors during the identifying step.

Another embodiment of the present invention includes a kit containing oligonucleotide primers for the short tandem repeat sequences.

A further embodiment includes a method for detecting polymorphic short tandem repeats comprising the steps of: determining non-duplicative nucleotide sequences of the formula $(A_wG_xT_yC_z)$ wherein A,G,T, and C represent the nucleotides; and w, x, y and z represent the number of each nucleotide in the sequence and range between 0 and 7 with the sum of $w+x+y+z$ ranging from 3 to 7; identifying and searching for $(A_wG_xT_yC_z)_n$ in databases containing known genetic sequences, wherein n represents the number of tandem repeats of the sequence and is at least about 5; extracting each nucleotide sequence and its flanking sequences found in the searching step; identifying the extracted sequences which have unique flanking sequences; synthesizing oligonucleotide primer pairs corresponding to the flanking sequences; performing PCR with the primer pairs on DNA samples from a test population; and examining the extension products from the PCR to detect polymorphic short tandem repeats.

Other and further objects, features and advantages will be apparent and the invention will be more readily understood from a reading of the following specification and by reference to the accompanying drawings, forming a part thereof, where examples of the presently preferred embodiments of the invention are given for the purpose of disclosure.

DESCRIPTION OF THE DRAWINGS

FIG. 3 shows examples of products from the multiplex and single PCR assays used in generating multilocus genotype data.

Figure 1:
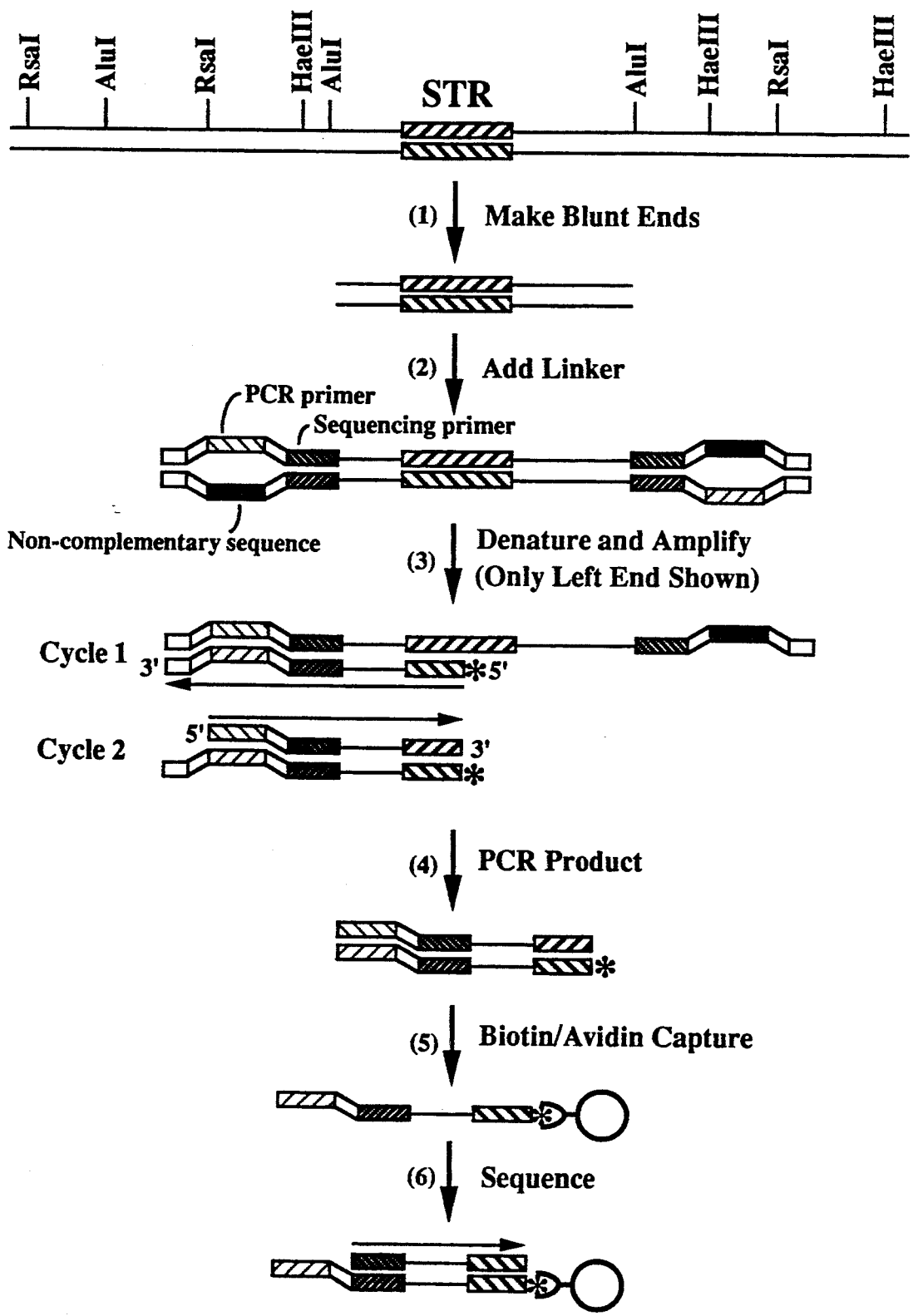
FIG. 1 illustrates the strategy used to determine the sequence flanking a STR.

The drawings and figures are not necessarily to scale and certain features of the invention may be exaggerated in scale or shown in schematic form in the interest of clarity and conciseness.

DETAILED DESCRIPTION OF INVENTION

It will be readily apparent to one skilled in the art that various substitutions and modifications may be made to the invention disclosed herein without departing from the scope and the spirit of the invention.

As used herein, the term "short tandem repeat" (STR) refers to all sequences between 2 and 7 nucleotides long which are tandemly reiterated within the human organism. The STRs can be represented by the formula $(A_wG_xT_yC_z)_n$ where A,G,T an C represent the nucleotides which can be in any order; w, x, y and z represent the number of each nucleotide in the sequence and range between 0 and 7 with the sum of $w+x+y+z$ ranging between 2 and 7; and n represents the number of times the sequence is tandemly repeated and is between about 5 and 50. Most of the useful polymorphisms usually occur when the sum of w+x+y+z ranges between 3 and 7 and n ranges between 5 and 40. For dimeric repeat sequences n usually ranges between 10 and 40.

As used herein "non-duplicative" sequence means the sequence and its complement. It is represented in its lowest alphabetical form as shown in Table 1. For example (ACT) represents ACT, CTA, TAC, AGT, TAG and GTA. Each representative sequence can represent a maximum of two times the number of nucleotides in the sequence.

As used herein "flanking sequence" refers to the nucleotide sequence on either side of the STR. "Unique flanking sequences" are those flanking sequences which are only found at one location within the genome.

The term "oligonucleotide primers" as used herein defines a molecule comprised of more than three deoxyribonucleotides or ribonucleotides. Its exact length will depend on many factors relating to the ultimate function and use of the oligonucleotide primer, including temperature, source of the primer and use of the method. The oligonucleotide primer can occur naturally, as in a purified restriction digest, or be produced synthetically. The oligonucleotide primer is capable of acting as an initiation point for synthesis when placed under conditions which induce synthesis of a primer extension product complementary to a nucleic acid strand. The conditions can include the presence of nucleotides and an inducing agent such as a DNA polymerase at a suitable temperature and pH. In the preferred embodiment, the primer is a single-stranded oligodeoxyribonucleotide of sufficient length to prime the synthesis of an extension product from a specific sequence in the presence of an inducing agent. Sensitivity and specificity of the oligonucleotide primers are determined by the primer length and uniqueness of sequence within a given sample of template DNA. In the present invention the oligonucleotide primers are usually about greater than 15 mer and in the preferred embodiment are about 20 to 30 mer in length.

Each pair of primers is selected to detect a different STR. Each primer of each pair herein is selected to be substantially complementary to a different strand in the flanking sequence of each specific STR sequence to be amplified. Thus one primer of each pair is sufficiently complementary to hybridize with a part of the sequence in the sense strand and the other primer of each pair is sufficiently complementary to hybridize with a different part of the same sequence in the antisense strand. Although the primer sequence need not reflect the exact sequence of the template, the more closely the 3' end reflects the exact sequence, the better the binding during the annealing stage.

As used herein the term "extension product" refers to the nucleotide sequence which is synthesized from the 3' end of the oligonucleotide primer and which is complementary to the strand to which the oligonucleotide primer is bound.

As used herein the term "differentially labeled" indicates that each extension product can be distinguished from all others because it has a different label attached and/or is of a different size and/or binds to a specifically labeled oligonucleotide. One skilled in the art will recognize that a variety of labels are available. For example, these can include radioisotopes, fluorescers, chemiluminescers, stains, enzymes and antibodies. Various factors affect the choice of the label. These include the effect of the label on the rate of hybridization and binding of the primer to the DNA, the sensitivity of the label, the ease of making the labeled primer, probe or extension products, the ability to automate, the available instrumentation, convenience and the like. For example, differential radioisotope labelling could include $^{32}P$, $^{3}H$ and $^{14}C$; differential fluorescers labelling could include fluorescein-5-isothiocyanate, tetramethylrhodamine-5- (and-6) isothiocyanate, Texas Red and NBD aminoheanoic acid; or a mixture of different labels such as radioisotopes, fluorescers and chemiluminescers.

Each specific, different DNA sequence, which is to be detected herein is derived from genomic DNA. The source of the genomic DNA to be tested can be any medical or forensic sample. Examples of medical and forensic samples include blood, semen, vaginal swabs, tissue, hair, saliva, urine and mixtures of body fluids. These samples can be fresh, old, dried and/or partially-degraded. The samples can be collected from evidence at the scene of a crime.

The term "forensic sample" as used herein means using the technology for legal problems including but not limited to criminal, paternity testing and mixed-up samples. The term "medical sample" as used herein means use of the technology for medical problems including but not limited to research, diagnosis, and tissue and organ transplants.

As used herein the term "polymorphism" refers to the genetic variation seen in the tandem repeats or flanking sequences. One example of this polymorphism is in the number of times the 3 to 7 nucleotide sequence is repeated.

As used herein the term "multiplex polymerase chain reaction" (mPCR) refers to a novel variation of PCR. It is a procedure for simultaneously performing PCR on greater than two different sequences. The mPCR reaction comprises: treating said extracted DNA to form single stranded complementary strands, adding a plurality of labeled paired oligonucleotide primers, each paired primer specific for a different short tandem repeat sequence, one primer of each pair substantially complementary to a part of the sequence in the sense strand and the other primer of each pair substantially complementary to a different part of the same sequence in the complementary antisense strand, annealing the plurality of paired primers to their complementary sequences, simultaneously extending said plurality of annealed primers from the 3' terminus of each primer to synthesize an extension product complementary to the strands annealed to each primer, said extension products, after separation from their complement, serving as templates for the synthesis of an extension product for the other primer of each pair, separating said extension products from said templates to produce single stranded molecules, amplifying said single stranded molecules by repeating at least once said annealing, extending and separating steps. In the mPCR process the preferred method for three loci includes: (1) primers composed of similar GC base compositions and lengths; (2) longer extension times up to 8 fold the normally utilized times; and (3) minimization of the number of PCR cycles performed to achieve detection for example approximately 23-25 cycles.

The mPCR reaction is optimized for each reaction. In some mPCR reactions the optimization further includes more enzyme than one normally adds to a PCR reaction.

As used herein, the term "match probability" refers to the chance that two unrelated persons will have the same combined genotype at the examined loci.

One embodiment of the present invention is a DNA profiling assay for detecting polymorphisms in a short tandem repeat, comprising the steps of: extracting DNA from a sample to be tested; amplifying the extracted DNA; and identifying said amplified extension products for each different sequence, wherein each different sequence has a differential label. Although a variety of known amplification procedures are known, the preferred embodiment employs PCR or mPCR.

In one embodiment of the present invention an external standard is used. In a preferred embodiment an internal standard is used. The internal standard is composed of labeled alleles of the STR loci of interest. One skilled in the art will recognize that the choice of standard and the intervals chosen will depend on the label and the desired resolution. For example, in a DNA profiling assay STR alleles from a DNA sample can be localized with greater than 1 bp resolution using an internal standard marker every 3-bp.

In a preferred assay, short tandem repeat sequences of nucleotides characterized by the formula $(A_wG_xT_yC_z)_n$ wherein A, G, T and C represent the nucleotides, w, x, y and z represent the number of each nucleotide and range from 0 to 7 and the sum of $w+x+y+z$ ranges from 3 to 7 and n represents the repeat number and ranges from 5 to 40 are used. In another preferred assay, the sum of $w+x+y+z$ is either 3 or 4. In the preferred embodiment of the profiling assay, at least two STRs are assayed simultaneously.

In the most preferred embodiment the DNA profiling assay is automated. This automation can be achieved by a variety of methods. One method is to use an automated DNA label analyzer capable of distinguishing simultaneously different fluorescers, radioactive labels or chemiluminescers during the identifying step. One skilled in the art will readily recognize that a variety of instrumentation meets this requirement. One example of such an analyzer used in the preferred assay is the Applied Biosystems 370A Fluorescent DNA sequence device ("370A device") which has the capability to distinguish between four different fluors during electrophoresis.

Another aspect of the present invention is a method of detecting polymorphic STRs for use in the DNA profiling assay. The method of detecting a polymorphic STR comprises the steps of: determining possible non-duplicative nucleotide sequences of the formula $(A_wG_xT_yC_z)$, wherein A, G, T and C represent each respective nucleotide and w, x, y and z represent the number of each nucleotide in the sequence and range between 0 and 7 with the sum of $w+x+y+z$ ranging between 2 and 7; searching for and identifying $(A_wG_xT_yC_z)_n$ in databases containing known genetic sequences and identifying the $(A_wG_xT_yC_z)_n$ sequence of said genetic sequence and its flanking sequence, wherein n represents the number of tandem repeats of the sequence and is at least about 5; extracting each identified sequence and its flanking sequence; identifying the extracted sequences which have unique flanking sequences; synthesizing oligonucleotide primer pairs to the unique flanking sequences; performing a PCR with the primer pairs on DNA samples from a test population; and examining the extension products of the PCR to detect polymorphic STRs.

A further aspect of the present invention is the provision of a kit for DNA profiling assays. The kit is comprised of a container having an oligonucleotide primer pairs for amplifying a STR. In the preferred embodiment the number of STR primer pairs is selected such that the genotype frequency (p) is at least $10^{-6}$. This usually requires 6–10 STR primer pairs.

A further addition to the kit can be a container having labelled standards. An additional enhancement to the kit is the addition of reagents for mPCR.

The following examples are offered by way of illustration and are not intended to limit the invention in any manner. In examples, all percentages are by weight, if for solids and by volume if for liquids, and all temperatures are in degrees Celsius unless otherwise noted.

EXAMPLE 1

Computer Identification of STR loci

STRs were identified by searching all human sequences in the GenBank DNA sequence repository for the presence of all possible classes of dimeric, trimeric, and tetrameric STRs. One skilled in the art will readily recognize that a similar search using repeats of 5 to 7 nucleotides can be used to identify STRs of 5 to 7 nucleotides in length. The possible non-duplicative nucleotide sequences used in this search are given by their lowest alphabetical representation.

TABLE 1

| Possible Non-Duplicative STRs | | | | | | | |
|---|---|---|---|---|---|---|---|
| (AA) | (AC) | (AG) | (AT) | (CC) | (CG) | | |
| (AAC) | (AAG) | (AAT) | (ACC) | (ACG) | (ACT) | (AGC) | (AGG) |
| (ATC) | (CCG) | (AAAC) | (AAAG) | (AAAT) | (AACC) | (AACG) | (AACT) |
| (AAGC) | (AAGG) | (AAGT) | (AATC) | (AATG) | (AATT) | (ACAG) | (ACAT) |
| (AGAT) | (ACCC) | (ACCG) | (ACCT) | (ACGC) | (ACGG) | (ACGT) | (ACTC) |
| (ACTG) | (ACTT) | (AGCC) | (AGCG) | (AGCT) | (AGGC) | (AGGG) | (ATCC) |
| (ATCG) | (ATGC) | (CCCG) | (CCGG) | | | | |

As shown in Table 2, the computer search identified a considerable number of STRs. The dimeric search was set to identify sequences in which the STR was repeated at least 10 times and the trimeric and tetrameric search was set to identify sequences which were repeated at least 5 times.

TABLE 2

| | HUMAN STRs IN THE GENBANK DNA | | |
|---|---|---|---|
| MONOMER LENGTH | DINUCLEO-TIDE (10 OR MORE) | TRINUCLEO-TIDE (5 OR MORE) | TETRA-NUCLEO-TIDE (5 OR MORE) |
| FRACTION OBSERVED | 5/6 | 10/10 | 16/34 |
| TOTAL NUMBER | 217 | 101 | 67 |

The fraction observed refers to the number of different classes of STRs observed out of the total number of possible STR classes. All classes of trimeric repeats were present and about half of the possible tetrameric sequences were represented.

Approximately 50% of STRs studied were polymorphic. Trimeric and tetrameric STRs have features of polymorphic markers useful for the physical and genetic mapping of the human genome and personal identification in the medical and forensic sciences.

EXAMPLE 2

Molecular Biological Identification of STR Loci

In addition to the procedure for identifying STRs in the GenBank, other methods are available to identify additional STR loci. For example, oligonucleotide probes for the possible 50 unique dimeric, trimeric and tetrameric STR sequences can be synthesized and used to screen total human DNA libraries. In one example recombinant bacteriophage lambda of the human X chromosome were plated at a density of 255 plaque forming units per 15 cm plate. Plaque lifts made from the plates are hybridized to $^{32}P$ 5' end-labeled oligonucleotides of the STR motifs. Standard hybridization methods were used. Oligonucleotides were labeled according to standard protocols.

With nucleotide sequences up to above 100 bp the conditions for hybridization may be estimated using the following formula:

$$T_i = T_m - 15° C.$$

$$T_m = 16.6 log[M] + 0.41[P_{gc}] + 81.5 - P_m - B/L - 0.6 - 5[P_f]$$

where:

M is the molar concentration of Na+, to a maximum of 0.5 (1×SSC contains 0.165 M Na+);

$P_{gc}$ is the percent of G or C bases in the oligonucleotide and is 1-16 between 30 and 70;

$P_m$ is the percent of mismatched bases, if known;

$P_f$ is the percent of formamide in the buffer;

B is 675 for synthetic probes up to 100 bases;

L is the length of the probe in bases.

The formula was used to arrive at the conditions in Table 3:

TABLE 3

| Oligo Id sequence | (ml) 2 × Hyb Mix | $P_f$(%) Formamide (ml) | H₂O (ml) | V (ml) |
|---|---|---|---|---|
| 1152 [AATC]₇.₅ | 12.5 | 10% 2.5 | 10 | 25 |
| 1154 [AGAT]₇.₅ | 12.5 | 10 2.5 | 10 | 25 |
| 1525 [AAT]₃₀ | 12.5 | 0 0 | 12.5 | 25 |
| 1526 [AATG]₇.₅ | 12.5 | 10 2.5 | 10 | 25 |
| 1528 [ACAG]₇.₅ | 12.5 | 30 7.5 | 5 | 25 |

The 2×hybridization mix contained 37.5 ml of 20×SSC, 15 ml of 50 X Denhardts, 7.5 ml of 20% SDS, and 15 ml of H₂O. Hybridizations were performed at 42° C.

These conditions were used to determine the frequency of each STR shown on the X chromosome using recombinant lambda from an X chromosome genomic library picked to a grid. (Table 4).

TABLE 4

| | The frequency of trimeric and tetrameric STRs. | |
|---|---|---|
| STR | Positive bacteriophage (%) | Frequency (kb/STR) |
| [AAT] | 5 | 300 |
| [AATC] | 5 | 300 |
| [AATG] | 3 | 500 |
| [ACAG] | 3 | 500 |
| [AGAT] | 3 | 500 |

A total of 1020 recombinant bacteriophage were hybridized to radiolabeled 30 bp oligonucleotides (e.g., [AATC]₇.₅). Calculations were based on an average insert size of 15 kb in the library. These hybridization results and the results from the GenBank studies suggest the presence of approximately 400 million STRs in the human genome. The X-chromosome results have been extended to the entire human genome by utilizing the complete genomic phage lambda library. Thus identification of sufficient STRs to extend the DNA typing assay to very high levels of individualization (e.g., one in a billion) is feasible.

EXAMPLE 3

Determination of DNA sequence flanking STRs

Clones containing STRs, for example M13, lambda, cosmid and YAC, can be identified by any procedure which allows hybridization to one of the core oligonucleotides. Most of the hybridization methods are usually laborious for determining the sequence of the unique DNA segments flanking both sides of the STR. In the present invention a strategy called STR-PCR was used. This strategy is shown in schematic form in (FIG. 1).

The STR-PCR strategy was based upon the method of Riley, et al, *Nucleic Acids Res.* 18: 2887 (1990). The Riley method was designed to amplify the ends of YAC molecules from total yeast genomic DNA. This method was adapted to amplify the DNA segments flanking STRs, and coupled to direct DNA sequencing of the products via a solid-phased--DNA sequencing technology. The procedure involves the following steps: (1) Blunt ends are generated to flank both sides of a STR in a cloned DNA segment by digestion with a single restriction enzyme. Multiple enzymes can be used, separately, to generate a flanking sequence length in the range of 100 to 150 bp. (2) A linker which contains a region of non-complementary DNA is ligated to the population of blunt ended molecules. (3) The flanking sequences are amplified in separate reactions. The left end is amplified with the anchored PCR primer and a primer of one strand of the STR. The right end is amplified with the same anchored PCR primer and a primer of the other strand of the STR. The STR primers may be biotinylated (*). (4) The final biotinylated (*) PCR product. (5) The biotinylated strand may be captured with avidin coated beads. And (6) The flanking sequence may be obtained by extension from the sequencing primer in the presence of dideoxynucleotides.

Figure 2A:
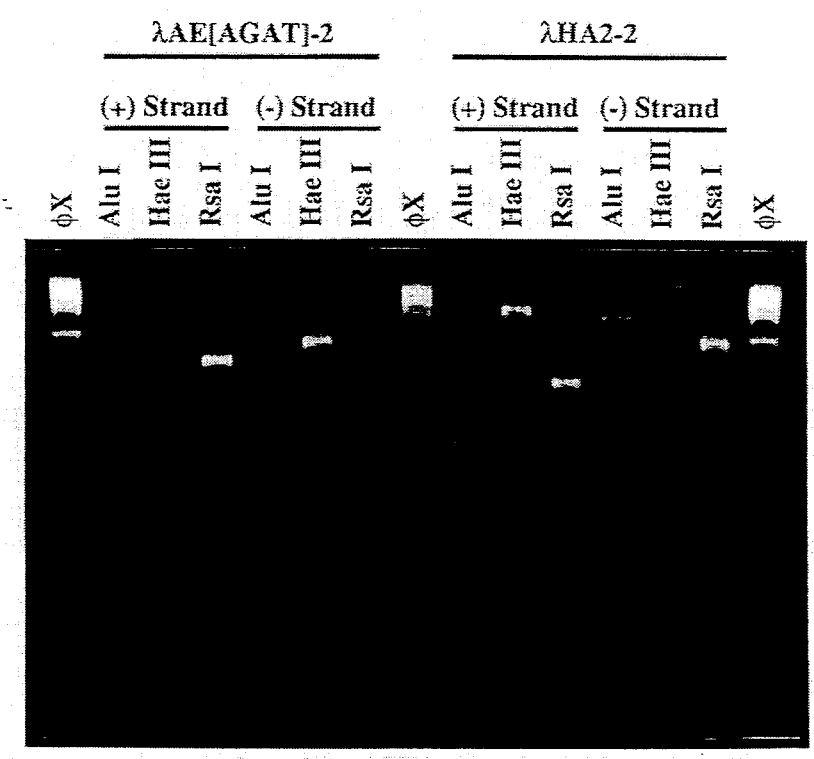
FIGS. 2A to 2C shows the development of a polymorphic STR locus.
Figure 2B:
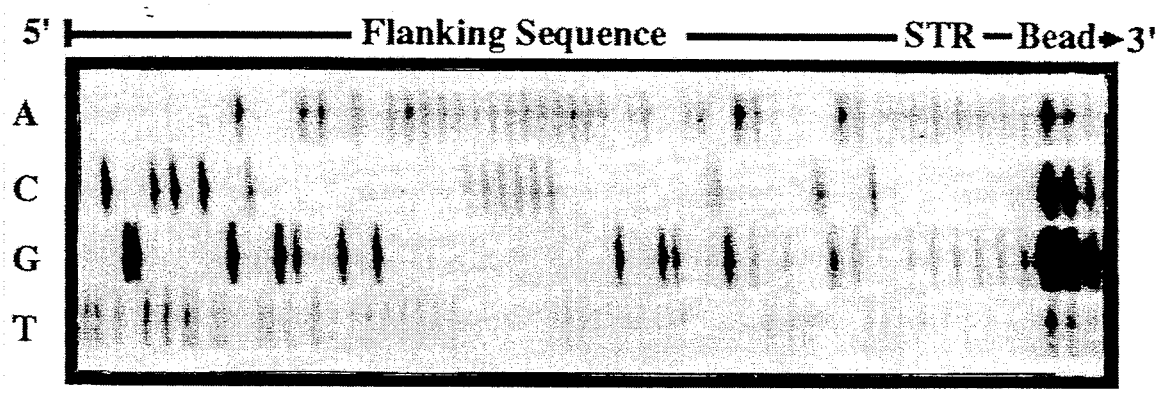
Figure 2C:
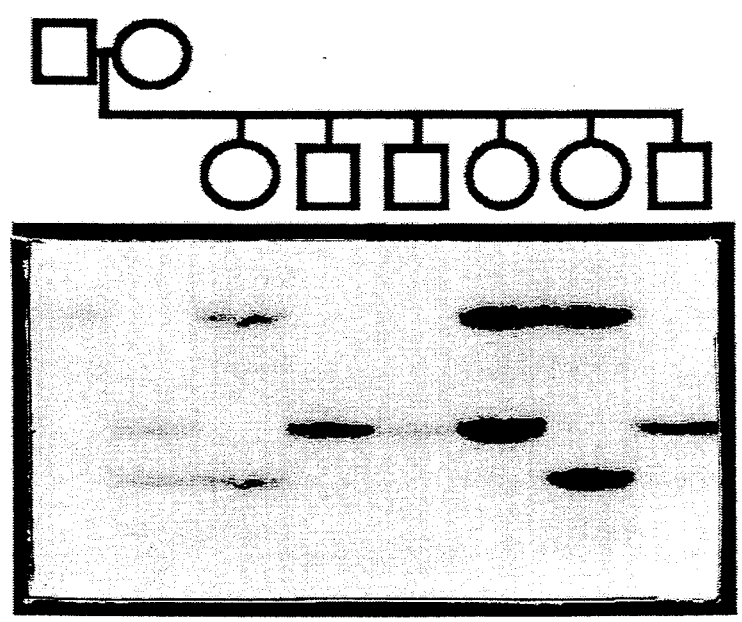

Results from using the STR-PCR strategy are shown in FIG. 2. Amplification of the DNA sequence flanking both sides of an (AGAT) STR from two recombinant bacteriophage is shown in FIG. 2A. While FIG. 2B shows direct DNA sequencing of single stranded template following capture and strand separation of the biotinylated amplification products of λAE[AGAT]-2 with avidin coated magnetic beads. FIG. 2C demonstrates the use of oligonucleotides complementary to the sequence flanking the STR to amplify the STR locus in a family.

Oligonucleotide primers which generate a blunt ended linker upon annealing were synthesized. Examples of these oligonucleotides are SEQ ID Nos: 1, 2, 3 and 4. Oligonucleotides (SEQ ID Nos: 1 and 2) form the double stranded linker, oligonucleotide (SEQ ID No: 3) is the PCR primer for the anchor and oligonucleotide (SEQ ID No: 4) is the DNA sequencing primer.

Oligonucleotide (SEQ ID No: 1) was phosphorylated and annealed to (SEQ ID No: 2) to form the double stranded linker by standard protocol. In this procedure 10 μL of one of the linker oligonucleotides (SEQ ID No: 1) (100 μM; 1 nanomole) is combined with about 10 μL of $^{32}$P-gamma-ATp (10 mM); about 5 μL of PNK buffer; about 3 μL of T4 PNKinase (30 U); about 22 μL of H$_2$O for about a 50 μL final volume (at about 37° C., for about 40 min.; and at about 65° C., for about 5 min). Then about 10 μL of the other linker oligonucleotide ( SEQ ID No: 2 ) (100 μM) is added. This mixture is held at about 95° C. for about 5 min. The mixture is then slowly cooled to room temperature.

Although the Riley method taught that both oligonucleotides should be phosphorylated, the present invention has discovered that it is sufficient and possibly better to phosphorylate only the first oligonucleotide.

The next procedure was to ligate the double stranded linker ( PCR anchor ) to recombinant bacteriophage lambda DNA. First each clone was digested with frequent cutting restriction enzymes which give blunt ends. For example: AluI, HaeIII, and RsaI. Second, the linker was ligated to the blunt ended DNA. Third, the flanking segments were amplified. In this procedure the sample was digested with sufficient enzyme to cut the DNA (about 0.5 μL Enzyme) in about 1.5 μL of One Phor All Plus Restriction Buffer (Pharmacia) about 250 ng Lambda Phage DNA (50 kb) and sufficient H$_2$O to bring the final volume to about 15 μL. The temperature was held at about 37° C. until the DNA was cut.

After the digestion, a cocktail for ligations is added. Although a variety of cocktails are known, the present invention used: up to about 2.0 μL of Annealed Oligonucleotides with about 0.05 μL of 1 M DTT, about 3.0 μL of 0.1 M rATP, about 0.25 μL of T4 DNA Ligase (Pharmacia), about 1.5 μL of One Phor All Plus Restriction Buffer and about 9.7 μL of H$_2$O. The mixture was held at about 15° C. for at least about 2 hours. Longer times, for example overnight, may give better results.

Next, the flanking segments were amplified. The amplification mix included about 3 μL of STR-PCR Primer (10×Cetus; 10 μM), about 3 μL of Anchor-PCR Primer (same as with STR-PCR primer), about 3 μL of dNTP mix (10×Cetus; 2 mM), about 3 μL of PCR Buffer (10×Cetus, without Mg++), about 3.0 μL of 0.01 M MgCl$_2$, about 1 μL of DNA, about 14.2 μL of H$_2$O, and about 0.3 μL of Amplitaq (Cetus).

The mixture was heated for about 2 min at about 95° C., then the PCR assay on the mixture included about 25–30 cycles of about 45 sec at about 95° C., then about 30 sec at about 60° C., then about 1 min at about 72° C. Finally, the mixture was held at about 72° C. for about 10 min, then transferred to about 4° C. In this procedure the STR-PCR was performed separately for both strands of the STR. Control of the concentration of Mg++ appeared to be important.

The amplified products were sequenced. If the STR primers are biotinylated (for example, by the Aminolink 2 methodology of Applied Biosystems, Inc. ) the products were captured with avidin coated beads (Dynal). The unwanted DNA strand was removed. The preferred conditions for isolation for the amplified products was as follows: about 25 μL of M280 Beads from Dynal were mixed with about 25 μL of PCR Product. This was held for about 30 min at about 25° C. on a rotating wheel. The supernatant was removed and about 150 μL of 0.15 M NaOH was added. This was held for 5 min. at about 25° C. The supernatant is then removed, the remaining material is washed at least once with H$_2$O and resuspended in about 7 μL of H$_2$O for DNA sequencing. Any standard DNA sequencing reactions can be used. In the present invention the sequencing was performed as for any single stranded template.

EXAMPLE 4

Frequency of PolymorDhic Variation of STRs and examples

Seventeen STRs present either within the human HPRT locus or in human sequences in the GenBank database were assayed for variation in the human population. Nine were polymorphic.

Amplifications were performed with Perkin-Elmer--Cetus thermocyclers, Amplitaq enzyme, and recommended buffer conditions in a volume of about 15 μL. Amplification conditions were about 95° C. for about 45 sec. , then about 60° C. for about 30 sec. , then about 72° C. for about 30 sec. Approximately 23–28 cycles were run. Amplified products were radiolabeled by inclusion of 2 μCi $_{32}$P-dCTP (3000 Ci/mmol) in the PCR. The HUM HPRTB [AGAT]$_n$ and HUMFABP [AAT]$_n$ loci, and the HUMRENA4 [ACAG]$_n$ and HUMTH01 [AATG]$_n$ loci, were studied as a multiplex PCR of two loci. Approximately 50 ng of genomic DNA was used in the PCRs. PCR products were diluted 2:5 in formamide, denatured at about 95° C. for about 2 min. , and loaded onto a DNA sequencing gel (about 6% (39:1) acrylamide: bisacrylamide, with about 7 M urea, and about 0.04% TEMED). Control reactions without added DNA were included in every set of amplifications. The amplification products ranged in size from between about 100 to 350 bp. This allowed precise determination of allele lengths.

The GenBank data for locus name, approximate repeat sequence, Primer SEQ ID No:, number of alleles observed, number of chromosomes studied and average predicted heterozygote frequencies are shown in Table 6.

TABLE 6

| | Example STR's | | | | |
|---|---|---|---|---|---|
| Locus and STR Sequence | PCR Primer SEQ. ID NO: | Alleles Detected | Chromosomes Studied | Heterozygotes (%) | Chromosomes |
| HUMFABP[AAT]$_{8-15}$ | 5,6 | 8 | 314 | 52–78 | 4 |
| HUMARA[AGC]$_{12-30}$ | 7,8 | 17 | 228 | 87–91 | X |
| HUMGPP3A09[AAGG]$_9$ | 9,10 | 4 | 24 | 31 | N.D. |
| HUMERP[c:AATG]$_2$[ACTC]$_4$ [c:AATG]$_5$ | 11,12 | 2 | 20 | 19 | 7 |

TABLE 6-continued

| | Example STR's | | | | |
|---|---|---|---|---|---|
| Locus and STR Sequence | PCR Primer SEQ. ID NO: | Alleles Detected | Chromosomes Studied | Heterozygotes (%) | Chromo- somes |
| HUMTH01[AATG]$_{6-12}$ | 13,14 | 7 | 320 | 72–78 | 11 |
| HUMTNFAB[AATG]$_5$ | 15,16 | 4 | 24 | 31 | 6 |
| HUMRENA4[ACAG]$_{7-12}$ | 17,18 | 6 | 310 | 34–48 | 1 |
| HUMHPRTB[AGAT]$_{9-16}$ | 19,20 | 8 | 227 | 69–78 | X |
| HUMSTRX1[AGAT]$_{13}$ | 21,22 | 11 | 44 | 60–84 | X |

In Table 6 the features of 9 polymorphic STR loci are shown. The range of heterozygote frequencies represents the values obtained for the least to most polymorphic racial group. Alleles from loci shown with a range of reiteration numbers (for example, HUMFABP-[AAT]$_{8-15}$) were sequenced to enable precise association of the number of tandem reiterations with specific alleles. The reiteration number of the GenBank clone is given for loci at which the range in the number of repeats is unknown. The lowest alphabetical representation of each STR motif is used, with the reverse complement (c:) indicated where appropriate for compound STR loci. Variability in the human population was assayed with a radioactive PCR assay.

EXAMPLE 5

Examples of data from the radioactive PCR assay for 5 STR loci

Figure 3A:
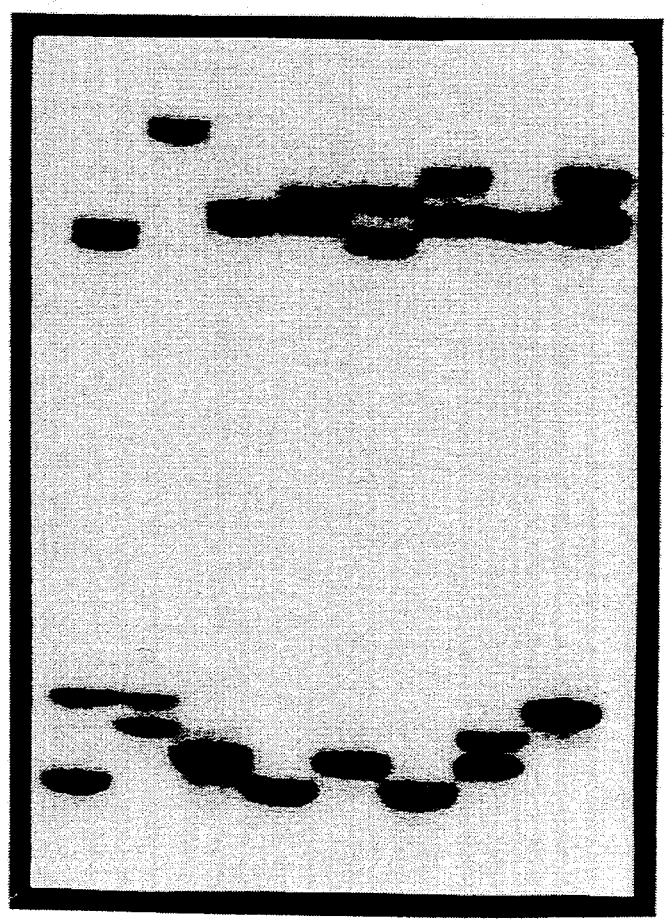
FIG. 3A shows the multiplex PCR(mPCR) of HUMHPRTB[AGAT]$_n$ (top) and HUMFABP[AAT]$_n$.
Figure 3B:
FIG. 3B shows the mPCR of HUMRENA4[ACAG]$_n$ (top) and HUMTH01[AATG]$_n$.
Figure 3C:
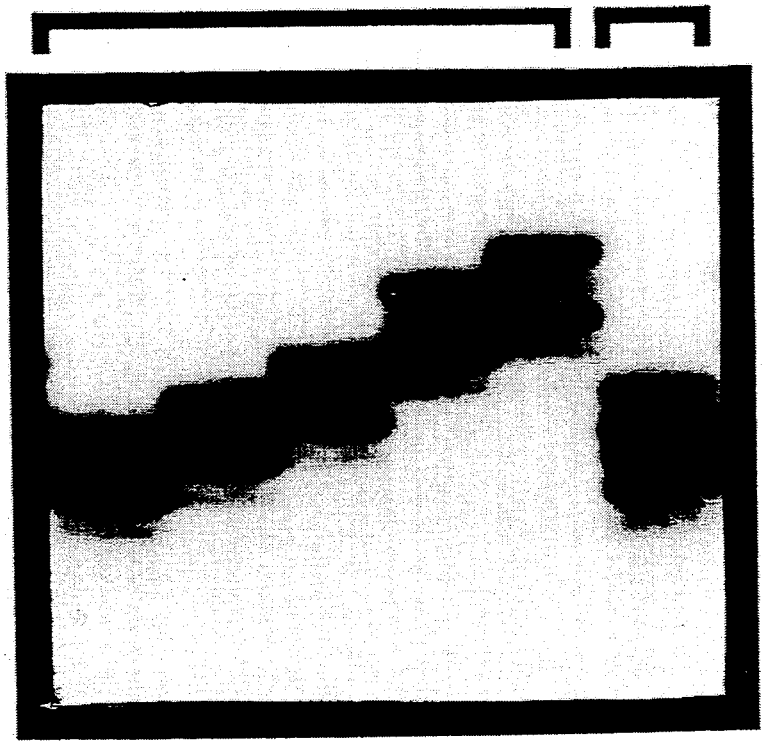
FIG. 3C shows the single PCR of HUMARA[AGC]$_n$.
Figure 4A:
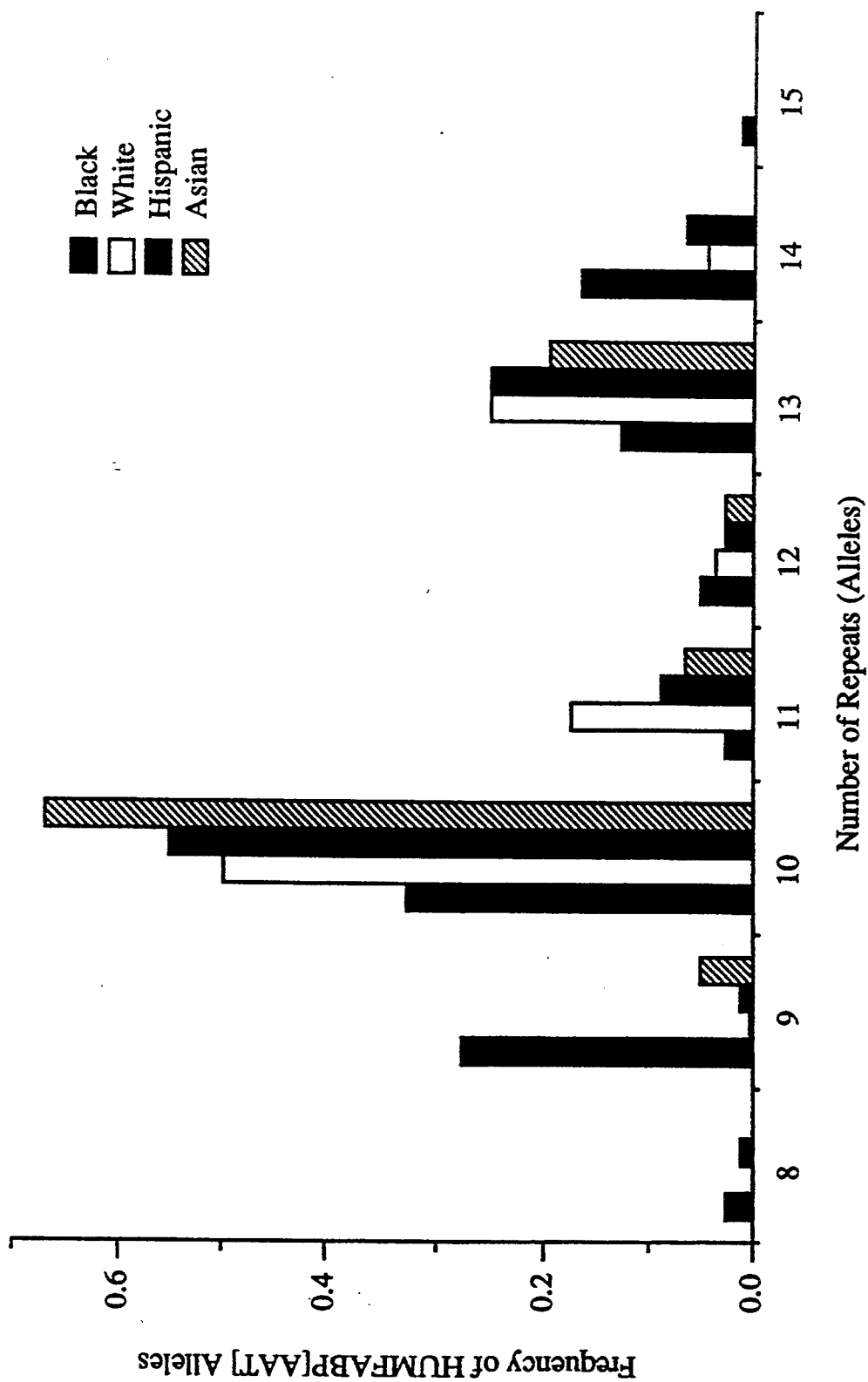
FIGS. 4A to 4E plot the relative allele frequency distributions. Allele counts were used to calculate and plot the relative frequencies of alleles at: 4A HUMRENA4[ACAG]$_n$; 4B HUMTH01[AATG]$_n$; 4C HUMARA[AGC]$_n$; 4D HUMHPRTB[AGAT]$_a$; and 4E HUMFABP[AAT]$_n$.
Figure 4B:
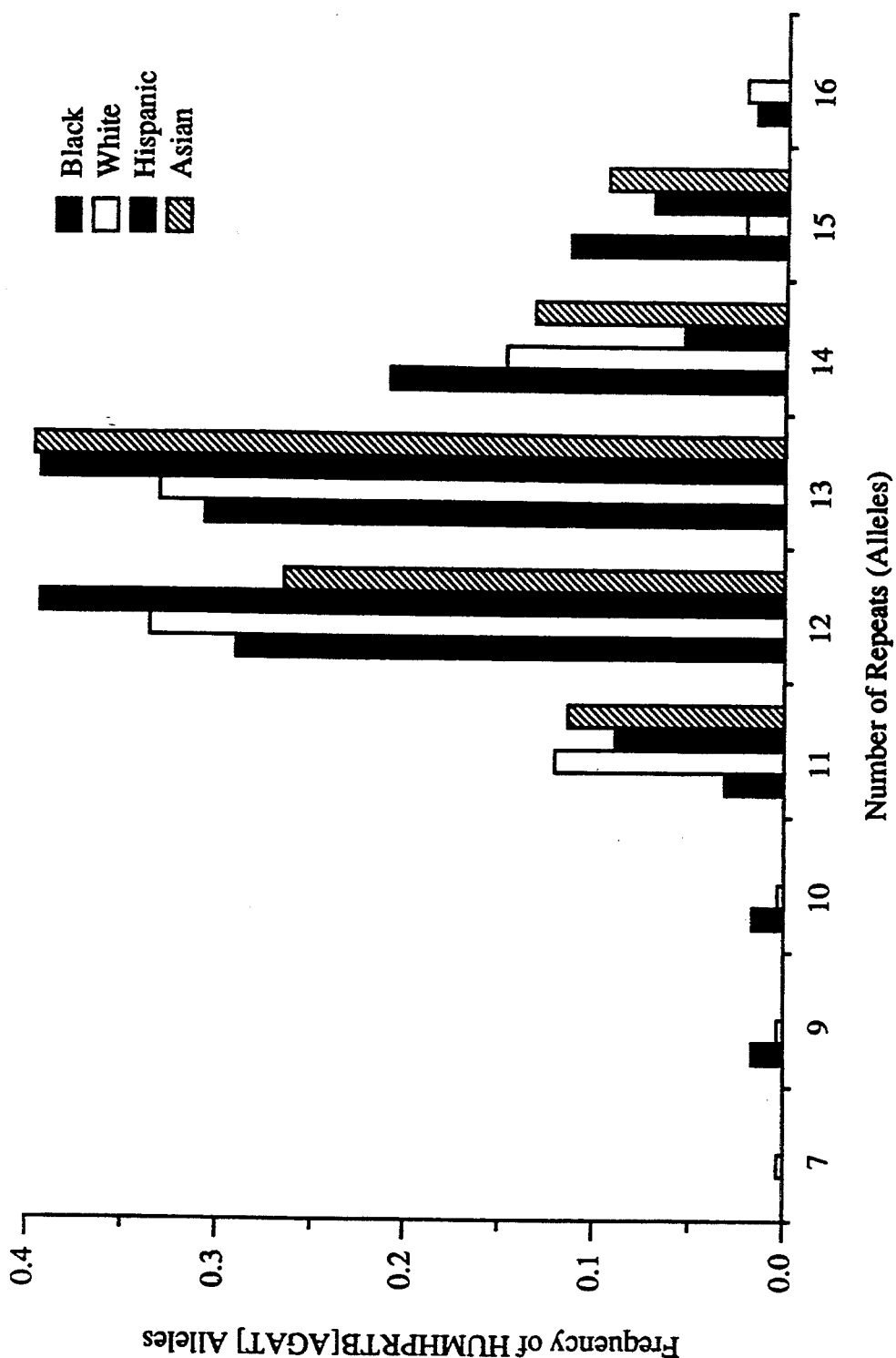
Figure 4C:
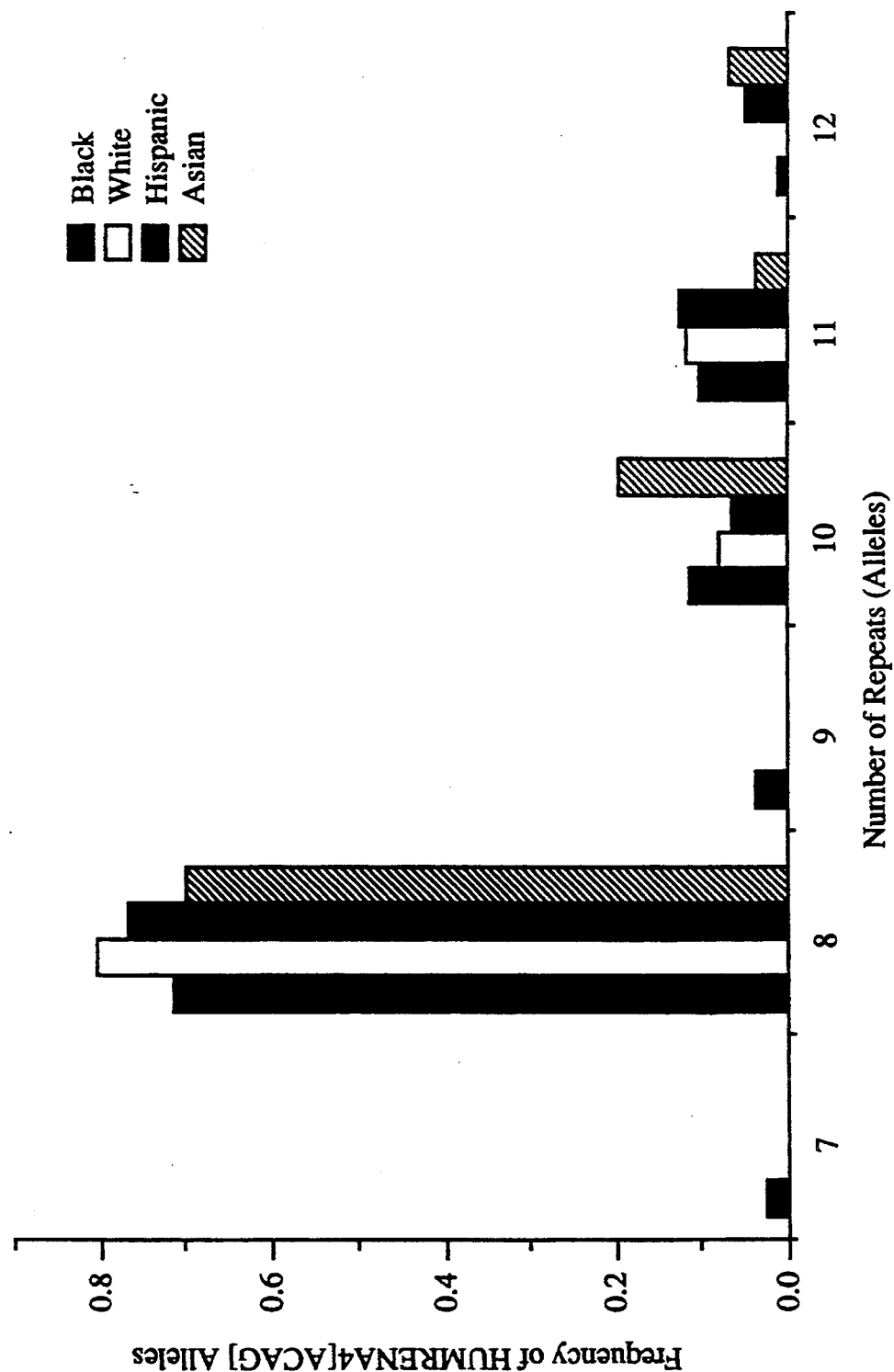
Figure 4D:
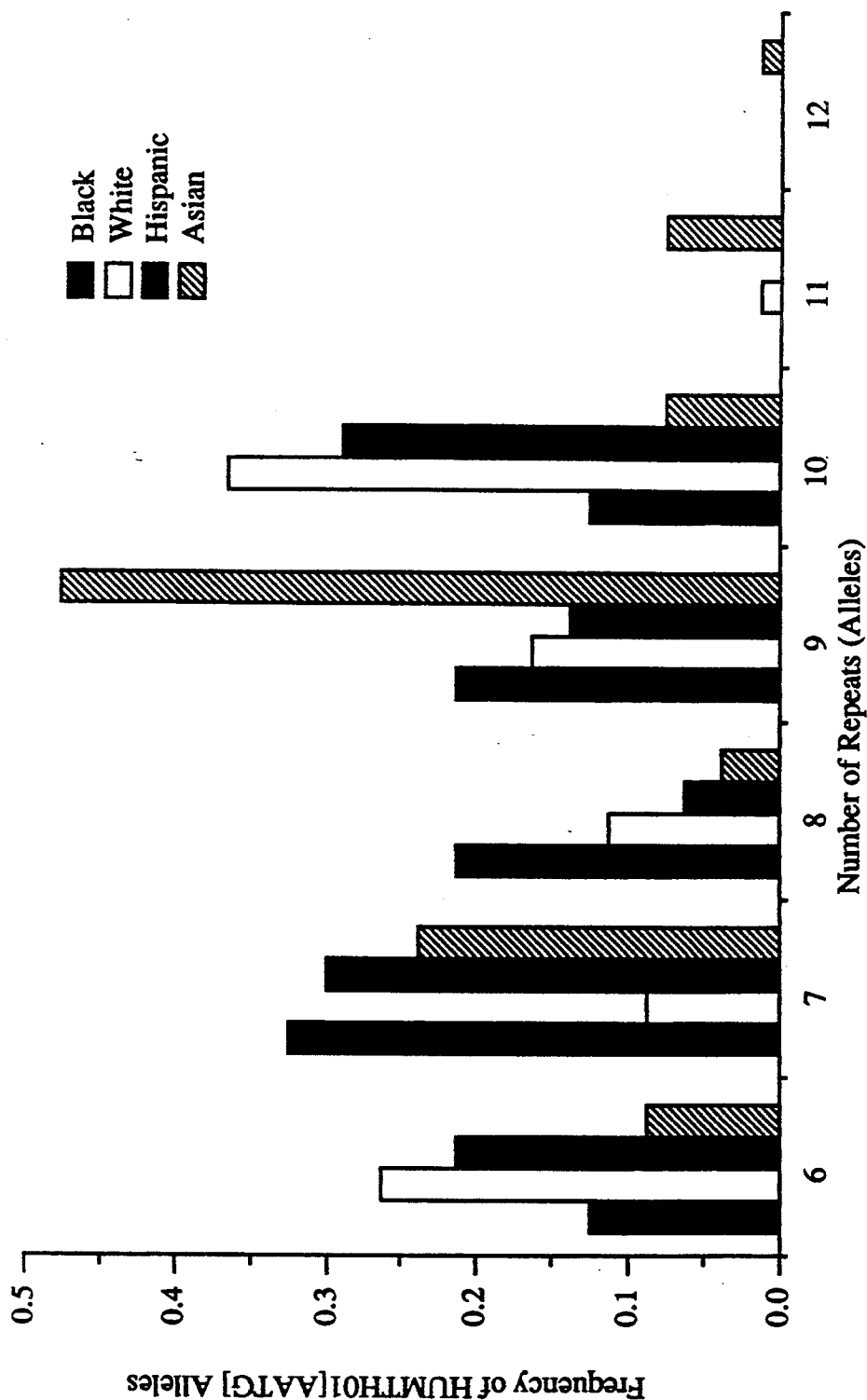
Figure 4E:
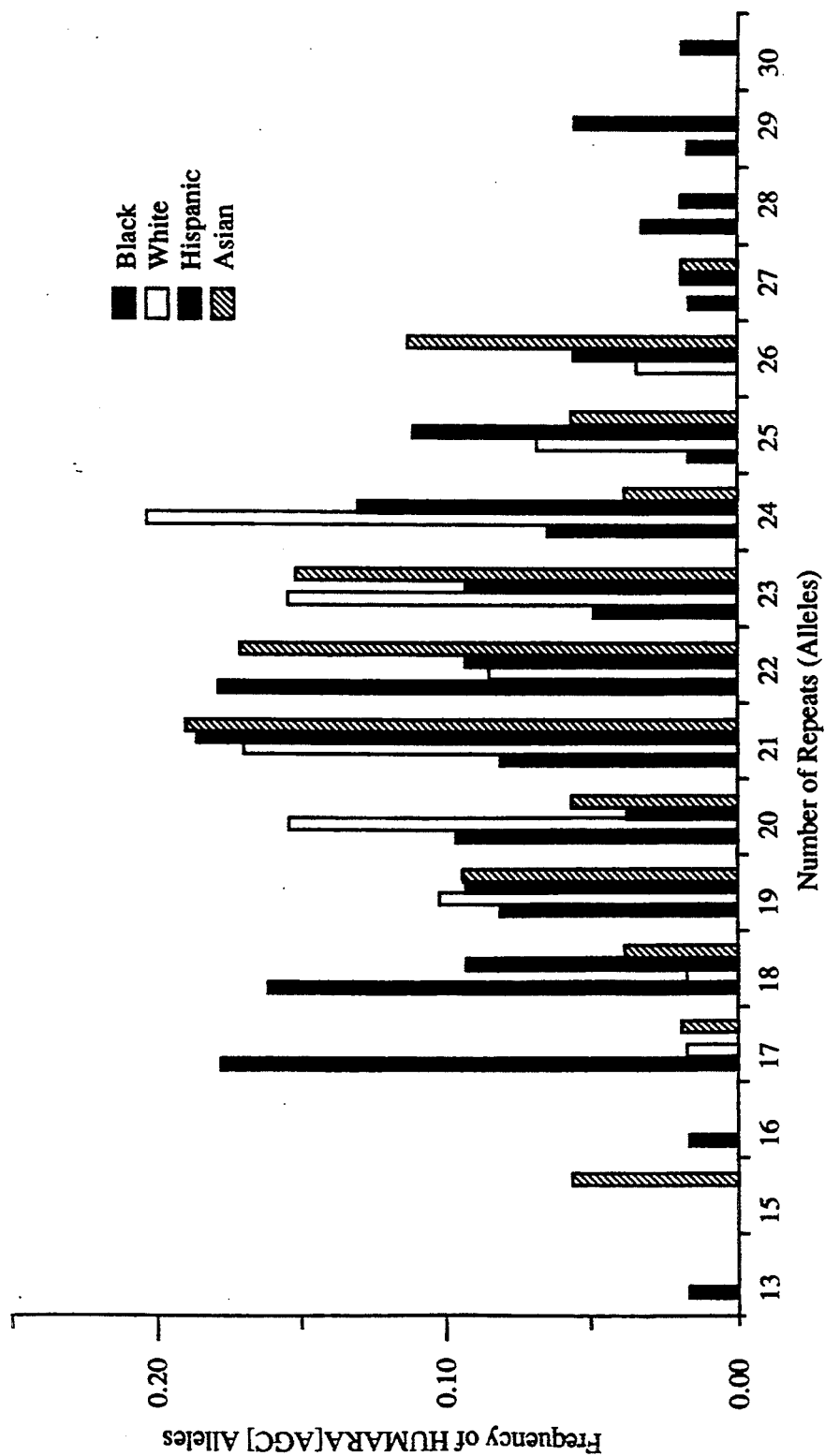

Genotype data for five STR loci were determined in two multiplex and one single PCR (FIG. 3). Both DNA strands of the amplified products are radiolabeled and the alleles of different loci have distinct appearances based on the relative mobilities of the two DNA strands. HUMHPRTB [AGAT]$_n$ and HUMTH01 [AATG]$_n$ alleles appear as closely spaced doublet bands, while HUMRENA4 [ACAG]$_n$ and HUMFABP [AAT]$_n$ alleles usually appear as singlets. HUMARA [AGC]$_n$ alleles appear as widely spaced doublets, such that adjacent alleles overlap. The faster strand of HUMHPRTB [AGAT]$_n$ alleles usually appear as a doublet, due to incomplete addition of an extra, non-complementary base to the 3' end of the product. The relative mobilities of the strands are influenced by the composition of the polyacrylamide gel. The data for Representative alleles from each of the polymorphic STRs were sequenced. The results show that the variation in size is a function of the number of repeats.

EXAMPLE 6

Population Genetics of STRs in four human ethnic groups

Trimeric and tetrameric STRs represent a rich source of highly polymorphic markers in the human genome. Analysis of a multilocus genotype survey of 40 or more individuals in U.S. Black, White, Hispanic, and Asian populations at five STR loci located on chromosomes 1, 4, 11, and X was performed. The heterozygote frequencies of the loci ranged from 0.34 to 0.91 and the number of alleles from 6 to 17 for the 20 race and locus combinations. Relative allele frequencies exhibited differences between races and unimodal, bimodal, and complex distributions. Genotype data from the loci were consistent with Hardy-Weinberg equilibrium by three tests and population sub-heterogeneity within each ethnic group was not detected by two additional tests. No mutations were detected in a total of 860 meiosis for two to five loci studied in various kindreds. An indirect estimate of the mutation rates give values from $2.5 \times 10^{-5}$ to $15 \times 10^{-5}$ for the five loci. Higher mutation rates appear to be associated with more tandem repeats of the core motif. The most frequent genotype for all five loci combined appears to have a frequency of $6.51 \times 10^{-4}$. Together, these results suggest that trimeric and tetrameric STR loci are ideal markers for understanding the mechanism of production of new mutations at hypervariable DNA regions and are suitable for application to personal identification in the medical and forensic sciences.

TABLE 7

| | Polymorphic Short Tandem Repeat Loci Studied | | | | |
|---|---|---|---|---|---|
| Locus and STR | Accession Number | Chromosome | PCR Primer SEQ. ID. NO: | Product Length (bp) | Gene |
| HUMFABP[AAT]$_n$ | M18079 | 4q31 | 5,6 | 199–220 | Intestinal Fatty Acid Binding Protein |
| HUMARA[AGC]$_n$ | M21748 | Xcen-q13 | 7,8 | 261–312 | Androgen Receptor |
| HUMTH01[AATG]$_n$ | D00269 | 11p15.5 | 13,14 | 183–207 | Tyrosine hydroxylase |
| HUMRENA4[ACAG]$_n$ | M10151 | 1q32 | 17,18 | 251–271 | Renin |
| HUMHPRTB[AGAT]$_n$ | M26434 | Xq26 | 19,20 | 263–299 | Hypoxanthine Phosphoribosyl transferase |

FIG. 3 was selected from the population surveys as a fair representation of the clarity with which allele designations were made. The autoradiograms were overexposed to illustrate the faint artifactual bands differing in the number of repeats which are thought to arise during the PCR.

SAMPLES

DNA was extracted from blood samples obtained at local blood banks from unrelated volunteer donors. Blood bank personnel visually designated donors as Black, White, or Other. Hispanics and Orientals were identified on the basis of surname. A total of 40 individuals in each of these four ethnic groups were studied.

Genotype data in 40 families (10 French, 27 Utah/Mormon, 2 Venezuelan, and 1 Amish) was determined with HUMHPRTB (AGAT)$_n$ and HUMFABP (AAT)$_n$. Five STR loci were studied in additional families for a minimum of 31 meiosis.

STR LOCI

The STR loci are designated by their GenBank locus name and the lowest alphabetical representation of the 44 possible unique trimeric and tetrameric repeat motifs. For example, HUMHPRTB (AGAT)$_n$ refers to the polymorphic (CTAT) STR located in intron 3 of the human hypoxanthine phosphoribosyltransferase (HPRT) gene. The loci studied, their GenBank accession numbers, chromosomal assignments, amplification primers, and range of product sizes (based on the GenBank sequence) are given in Table 7.

In Table 8 the alleles are numbered according to the number of tandem repeats present in the amplification products. The number of repeated motifs was determined by direct DNA sequencing of amplified products or by subcloning into M13 for sequencing. The repeat number of subcloned fragments was verified relative to the original genomic DNA source by amplification of the cloned segment.

COMPUTATIONS AND STATISTICS

A variety of standard population genetics tests were employed to evaluate the heterozygote frequencies, allele frequencies and random association of alleles at different loci. These tests included measurements of standard errors, G-statistics for the likelihood-ratio test, binomal distributions, Hardy-Weinberg equilibrium and the summary statistic ($S_k^2$).

RELATIVE ALLELE FREQUENCIES

Allele frequencies and their standard errors were calculated from the genotypes of approximately 40 individuals for the 20 combinations of five STR loci and four populations (Table 8).

TABLE 8

| Allele Frequencies and Their Standard Errors at Five STR Loci in Four Populations | | | | | |
|---|---|---|---|---|---|
| | Allele frequencies (%) and standard errors (%) in Allele[a] | | | | |
| | Whites | Blacks | Hispanics | Asians | Pooled[b] |
| LOCUS - HUMHPRTB[AGAT]$_n$ | | | | | |
| 7  | 0.4 ± 0.4 | —[c] | — | — | 0.3 ± 0.3 |
| 9  | 0.4 ± 0.4 | 1.6 ± 1.6 | — | — | 0.5 ± 0.4 |
| 10 | 0.4 ± 0.4 | 1.6 ± 1.6 | — | — | 0.5 ± 0.4 |
| 11 | 12.1 ± 2.2 | 3.2 ± 2.2 | 8.9 ± 3.8 | 11.3 ± 4.4 | 10.1 ± 1.5 |
| 12 | 34.4 ± 3.2 | 29.0 ± 5.8 | 39.3 ± 6.5 | 26.4 ± 6.1 | 33.2 ± 2.4 |
| 13 | 33.0 ± 3.1 | 30.6 ± 5.9 | 39.3 ± 6.5 | 39.6 ± 6.7 | 34.4 ± 2.4 |
| 14 | 14.7 ± 2.4 | 21.0 ± 5.2 | 5.4 ± 3.0 | 13.2 ± 4.7 | 14.2 ± 1.8 |
| 15 | 2.2 ± 1.0 | 11.3 ± 4.0 | 7.1 ± 3.4 | 9.4 ± 4.0 | 5.3 ± 1.1 |
| 16 | 2.2 ± 1.0 | 1.6 ± 1.6 | — | — | 1.5 ± 0.6 |
| (n[d]) | 224 | 62 | 56 | 53 | 395 |
| LOCUS - HUMTH01[AATG]$_n$ | | | | | |
| 6  | 26.2 ± 4.9 | 12.5 ± 3.7 | 21.3 ± 4.6 | 8.8 ± 3.2 | 17.2 ± 2.1 |
| 7  | 8.8 ± 3.2 | 32.5 ± 5.2 | 30.0 ± 5.1 | 23.7 ± 4.8 | 23.8 ± 2.4 |
| 8  | 11.3 ± 3.5 | 21.3 ± 4.6 | 6.3 ± 2.7 | 3.8 ± 2.1 | 10.6 ± 1.7 |
| 9  | 16.2 ± 4.1 | 21.3 ± 4.6 | 13.7 ± 3.9 | 47.5 ± 5.6 | 24.7 ± 2.4 |
| 10 | 36.2 ± 5.4 | 12.5 ± 3.7 | 28.7 ± 5.1 | 7.5 ± 2.9 | 21.3 ± 2.3 |
| 11 | 1.3 ± 1.2 | — | — | 7.5 ± 2.9 | 2.2 ± 2.3 |
| 12 | — | — | — | 1.3 ± 1.2 | 0.3 ± 0.3 |
| (n) | 80 | 80 | 80 | 80 | 320 |
| LOCUS - HUMRENA4[ACAG]$_n$ | | | | | |
| 7  | — | 2.5 ± 1.7 | — | — | 0.6 ± 0.5 |
| 8  | 80.3 ± 4.6 | 71.2 ± 5.1 | 76.2 ± 4.8 | 69.7 ± 5.3 | 74.4 ± 2.5 |
| 9  | — | 3.8 ± 2.1 | — | — | 1.0 ± 0.6 |
| 10 | 7.9 ± 3.1 | 11.3 ± 3.5 | 6.3 ± 2.7 | 19.7 ± 4.6 | 11.2 ± 1.8 |
| 11 | 11.8 ± 3.7 | 10.0 ± 3.4 | 12.5 ± 3.7 | 3.9 ± 2.2 | 9.6 ± 1.7 |
| 12 | — | 1.3 ± 1.2 | 5.0 ± 2.4 | 6.6 ± 2.8 | 3.2 ± 1.0 |
| (n) | 76 | 80 | 80 | 76 | 312 |
| LOCUS - HUMPABP[AAT]$_n$ | | | | | |
| 8  | — | 2.5 ± 1.7 | 1.3 ± 1.2 | — | 0.6 ± 0.3 |
| 9  | 0.3 ± 0.3 | 27.5 ± 5.0 | 1.3 ± 1.2 | 5.1 ± 2.5 | 5.2 ± 1.0 |
| 10 | 49.7 ± 2.9 | 32.5 ± 5.2 | 55.0 ± 5.6 | 66.7 ± 5.3 | 50.4 ± 2.2 |
| 11 | 17.4 ± 2.2 | 2.5 ± 1.7 | 8.8 ± 3.2 | 6.4 ± 2.8 | 12.3 ± 1.4 |
| 12 | 3.4 ± 1.0 | 5.0 ± 2.4 | 2.5 ± 1.7 | 2.6 ± 1.8 | 3.4 ± 0.8 |
| 13 | 24.8 ± 2.5 | 12.5 ± 3.7 | 25.0 ± 4.8 | 19.2 ± 4.4 | 22.2 ± 1.8 |
| 14 | 4.4 ± 1.2 | 16.3 ± 4.1 | 6.2 ± 2.7 | — | 5.8 ± 1.0 |
| 15 | — | 1.3 ± 1.2 | — | — | 0.2 ± 0.2 |
| (n) | 298 | 80 | 80 | 78 | 536 |
| 0 | | | | | |
| LOCUS - HUMARA[AGC]$_n$ | | | | | |
| 13 | — | 1.6 ± 1.6 | — | — | 0.4 ± 0.4 |
| 15 | — | — | — | 5.7 ± 3.2 | 1.3 ± 0.8 |
| 16 | — | 1.6 ± 1.6 | — | — | 0.4 ± 0.4 |
| 17 | 1.7 ± 1.7 | 17.7 ± 4.9 | — | 1.9 ± 1.9 | 5.7 ± 1.5 |
| 18 | 1.7 ± 1.7 | 16.1 ± 4.7 | 9.3 ± 3.9 | 3.8 ± 2.6 | 7.9 ± 1.8 |
| 19 | 10.2 ± 3.9 | 8.1 ± 3.5 | 9.3 ± 3.9 | 9.4 ± 4.0 | 9.2 ± 1.9 |
| 20 | 15.3 ± 4.7 | 9.7 ± 3.8 | 3.7 ± 2.6 | 5.7 ± 3.2 | 8.8 ± 1.9 |
| 21 | 16.9 ± 4.9 | 8.1 ± 3.5 | 18.5 ± 5.3 | 18.9 ± 5.4 | 15.4 ± 2.4 |
| 22 | 8.5 ± 3.6 | 17.7 ± 4.9 | 9.3 ± 3.9 | 17.0 ± 5.2 | 13.6 ± 2.3 |
| 23 | 15.3 ± 4.7 | 4.8 ± 2.7 | 9.3 ± 3.9 | 15.1 ± 4.9 | 11.0 ± 2.1 |
| 24 | 20.3 ± 5.2 | 6.5 ± 3.1 | 13.0 ± 4.6 | 3.8 ± 2.6 | 10.5 ± 2.0 |

TABLE 8-continued

Allele Frequencies and Their Standard Errors at Five STR Loci in Four Populations

| | Allele frequencies (%) and standard errors (%) in Allele[a] | | | | |
|---|---|---|---|---|---|
| | Whites | Blacks | Hispanics | Asians | Pooled[b] |
| 25 | 6.8 ± 3.3 | 1.6 ± 1.6 | 11.1 ± 4.3 | 5.7 ± 3.2 | 6.1 ± 1.6 |
| 26 | 3.4 ± 2.4 | — | 5.6 ± 3.1 | 11.3 ± 4.3 | 4.8 ± 1.4 |
| 27 | — | 1.6 ± 1.6 | 1.8 ± 1.8 | 1.9 ± 1.9 | 1.3 ± 0.8 |
| 28 | — | 3.2 ± 2.2 | 1.8 ± 1.8 | — | 1.3 ± 0.8 |
| 29 | — | 1.6 ± 1.6 | 5.6 ± 3.1 | — | 1.8 ± 0.9 |
| 30 | — | — | 1.8 ± 1.8 | — | 0.4 ± 0.4 |
| (n) | 59 | 62 | 54 | 53 | 228 |

[a]Allelic designations refer to the number of repeats of the core sequence motif indicated in the locus column.

Frequencies of some specific alleles (for example, allele 7 of HUMTH01 [AATG]$_n$ and allele 17 of HUMARA [AGC]$_n$) are clearly variable across the four racial groups. Allele frequency distributions by race are given in FIG. 4. With the exception of HUMHPRTB (AGAT)$_n$, which is unimodal and symmetrical, the allele frequency distributions appear bimodal or more complex. The most common allele, however, appears to be the same for some loci (for example, HUMRENA4 (ACAG)$_n$), while at other loci predominant alleles do not coincide between races (for example, HUMARA (AGC)$_n$).

MOST FREQUENT GENOTYPES

The frequencies of the most common genotypes of a DNA typing system reflect the utility of that assay in practice. The most frequent genotypes for the five STR loci have frequencies from 0.048 to 0.645 in the 20 STR-race combinations (Table 9). The most common genotypes for all five loci combined (p) have frequencies from $1.40 \times 10^{-4}$ to $6.54 \times 10^{-4}$ in the four racial groups.

TABLE 9

| Most Frequent Genotype at the Five STR Loci in Four Populations | | | | | |
|---|---|---|---|---|---|
| Locus | Whites | Blacks | Hispanics | Asians | Pooled |
| HUMHPRTB[AGAT]$_a$ | 0.227 | 0.177 | 0.309 | 0.209 | 0.228 |
| HUMTH01[AATG]$_a$ | 0.190 | 0.138 | 0.172 | 0.225 | 0.118 |
| HUMRENA4[ACAG]$_a$ | 0.645 | 0.507 | 0.581 | 0.486 | 0.553 |
| HUMFABP[AAT]$_a$ | 0.247 | 0.179 | 0.303 | 0.445 | 0.254 |
| HUMARA[AGC]$_n$ | 0.069 | 0.063 | 0.048 | 0.064 | 0.042 |
| Combined (P) | $4.74 \times 10^{-4}$ | $1.40 \times 10^{-4}$ | $4.49 \times 10^{-4}$ | $6.51 \times 10^{-4}$ | $1.69 \times 10^{-4}$ |
| P$^2$ | $2.25 \times 10^{-7}$ | $1.96 \times 10^{-8}$ | $2.02 \times 10^{-7}$ | $4.24 \times 10^{-7}$ | $2.52 \times 10^{-8}$ |

The match probability (P$^2$) for the most common genotype of all five loci combined was $4.24 \times 10^{-7}$. The frequencies of the least common genotypes for all five loci combined were on the order of $10^{-17}$. The probability calculations in Table 15 are only relevant for female individuals since two of the loci are X-linked. The most common male genotypes for all five loci combined have frequencies from $6.78 \times 10^{-4}$ to $36.4 \times 10^{-4}$ in the four racial groups.

The best markers for individualization in medicine and forensic science may be those with symmetrical and similar allele frequency distributions. Choice of the proper ethnic database appears less critical at such loci for the four ethnic populations we have studied.

The faint artifactual bands which are thought to arise during the PCR, assist in genotype determination relative to external standards. It is possible to count between lanes from allele to allele on overexposed autoradiograms such that even widely separated alleles differing by approximately 6 repeat units were accurately scored. The use of mPCR with fluorescent labels and internal standards improves upon this accuracy.

The data demonstrate that genotype data from trimeric and tetrameric tandem repeats were accurately and efficiently obtained via multiplex PCR. The fidelity with which trimeric and tetrameric STRs were amplified compared to the dimeric STRs make these new class of polymorphic markers well suited for application to DNA typing in forensic science and medicine.

EXAMPLE 7

Fluorescent DNA Profiling Assay With Internal Standards

DNA typing is a powerful technique for determining the relationship, if any, between two genomic DNA samples. Applications for DNA typing include personal identification in paternity testing and forensic science, and sample source determinations in transplantation, prenatal diagnosis, and pedigree validation. Several features of polymorphic STRs suggest that they could form the basis of a powerful and simple DNA typing assay. The small size of the amplified units allows several loci to be easily amplified simultaneously by mPCR, and analyzed with precise allele identification on DNA sequencing gels. The precision, sensitivity, and speed of detecting alleles with PCR offers special opportunities for the study of forensic specimens. For example, trimeric and tetrameric STRs show excellent fidelity of amplification indicating that the genotyping fingerprints can be easily interpreted and are amenable to automation. Fluorescent DNA fragment detection can be used for internal size standards and precise allele quantitation.

Figure 5:
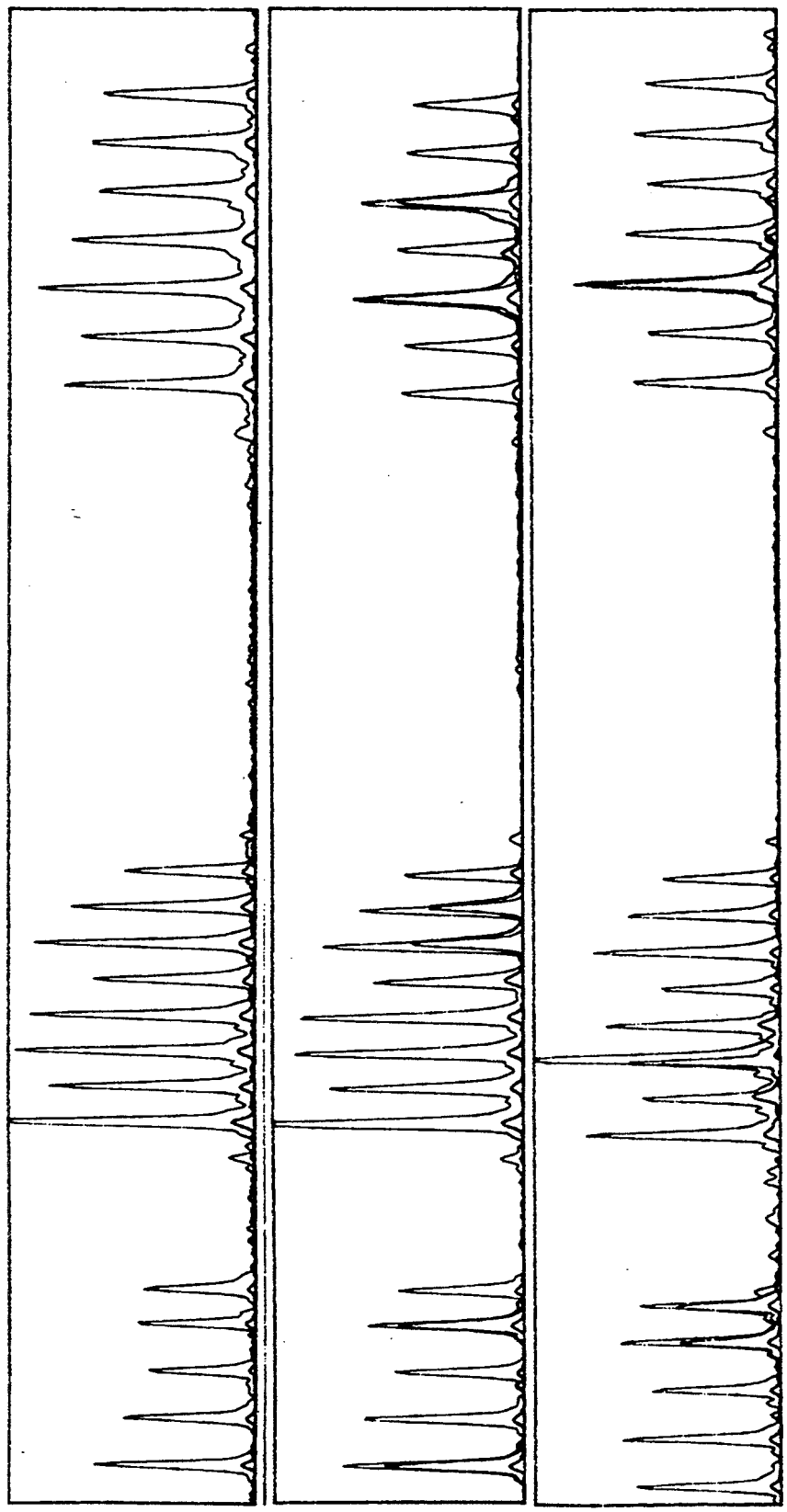
FIG. 5 shows the results of a fluorescent DNA typing assay. The analysis software scales the intensities of the fluorescent profiles relative to the strongest signal.

For genetic typing, alleles from three chromosomally unlinked STR loci were amplified simultaneously in a mPCR (FIG. 5). One primer from each of the three amplification primer sets is differentially labeled with one of the four fluorescent dyes used with the DNA sequencing device. In the ABI 370A system, one dye is reserved for the internal standards, while three dyes are available for the amplification products of STR loci. Theoretically, any given region of the sequencing gel can contain internal standards as well as alleles from three unlinked STR loci. Used to full potential the approach has enormous personal identification power of high accuracy.

Amplification incorporates a fluorescent label into one end, and a MluI site into the other end of each product in the mPCR (FIG. 5). Following amplification of the STR loci from a genomic DNA sample, residual activity of the *T. aquaticus* polymerase is destroyed and a homogeneous fragment length is achieved for each allele by digestion with M1uI. The treated multiplex products are then mixed with internal standards and loaded onto a sequencing gel for analysis on an ABI 370A.

Internal standards were generated by pooling amplification products from individuals of known genotype such that the molar ratios of each allele observed were approximately equal. The pooled alleles were diluted, reamplified, and treated with MluI. This scheme for generating internal standard size markers insures a virtually unlimited supply of standards.

The combination of a quantitative detection system and mPCR enabled additional levels of internal control and precision. Using mPCR products synthesized under standardized amplification conditions, the fluorescent intensity of specific alleles at different loci was related. Because of the relationship between alleles of different loci, it was possible to distinguish between homozygosity and hemizygosity at a given locus (FIG. 5). While failure of allele amplification can occur by primer binding site polymorphism, the null was detectable by quantitation. This quantitative capacity removes the doubt which has been cast on the use of VNTRs due to the observation of homozygosity excess in population studies. The quantitative nature of the allele identification also facilitated the analysis of mixed body samples which occurs in forensics, prenatal diagnosis, the detection of chromosomal aneuploidy, and true somatic mosaicism seen in patients with chromosomal abnormalities and following bone marrow transplantation.

The average individualization potential ($P_1$) of the three loci together was one in 500 individuals. The combined genotype frequencies (three loci) of the individuals in panels A and B were 0.00026 and 0.0085 assuming Hardy-Weinberg equilibrium. The addition of three more loci will give a $P_1$ of approximately one in 200,000, while the addition of six more loci will give a $P_1$ of one in 90 million. Multiplex PCRs of this complexity have been done. Eight and nine genetic site mPCR for the hypoxanthine phosphoribosyltransferase and dystrophin genes are known.

Oligonucleotides were synthesized on an Applied Biosystems (ABI) 380B DNA synthesizer. Underivatized oligonucleotides were not purified after deprotection and lyophilization. ABI Aminolink 2 chemistry was used to derivatize oligonucleotides for biotin and fluorescent labeling, after which they were ethanol precipitated and purified by polyacrylamide gel electrophoresis. The fluorescent dyes (Molecular Probes, Eugene, OR) used in the assay were (i) NBD aminoheanoic acid for all internal standard markers, (ii) 5-(and-6)-carboxyfluorescein succinimidyl ester for the HUMTH01 [AATG]$_n$ and HUMHPRTB [AGAT]$_n$ loci, and (iii) Texas Red ™ sulfonyl chloride for the HUMFABP [AAT]$_n$ locus. The primer sets had the first primer derivatized and the second primer containing an M1uI restriction site. The primers used were: HUMTH01 (AATG)$_n$, (SEQ. ID NOS: 13, 23); ;HUMFABP(ATT)$_n$ (SEQ ID NOS; 5, 24); HUMHPRTB (AGAT)$_n$ (SEQ ID. NOS; 19, 25). Simultaneous amplification with all six primers was performed with 25 cycles by denaturing at about 95° C. for about 45 sec., annealing at about 60° C. for about 30 sec., and extending at about 72° C. for about 30 sec. using Perkin-Elmer-Cetus thermocyclers, amplitaq, and buffer conditions. The concentration of primers in the multiplex were about 0.06 μM for HUMTH01 [AATG]$_n$, about 1.6 μM for HUMFABP [AAT]$_n$ and about 0.56 μM for HUMHPRTB [AGAT]$_n$. Following amplification, the products were phenol extracted, ethanol precipitated, and digested with M1uI. The digested multiplex products were then combined with the internal size standards and electrophoresed through a 6.5% polyacrylamide, 8.3 M urea gel at 1300–1500 V, 24 mA and 32 W at a temperature of about 46° C. Internal size standards were prepared by amplifying specific alleles from individuals of known genotype. The products were quantitated, combined to give near equimolarity, diluted approximately 5000 fold, and reamplified with approximately 12 cycles.

In FIG. 5A, fluorescent profiles of the internal standard cocktails when combined and electrophoresed in a single lane of an ABI 370A DNA sequencing device are shown. In FIG. 5B the internal standards were combined with the amplification products of a multiplex PCR composed of (left to right) the HUMTH01 (AATG)$_n$, (I), HUMFABP (AAT)$_n$ (II), and HUMHPRTB (AGAT)$_n$ (III) loci. The individual shown is heterozygous for all three markers. In FIG. 5C multiplex amplification from an individual homozygous at the HUMFABP (AAT)$_n$ locus and hemizygous at HUMHPRTB (AGAT)$_n$ is shown.

EXAMPLE 8

Alternative Detection Schemes: Radioactive, Silver Stain, Intercalation

Since some forensic laboratories may not have access to fluorescent detection devices, the STR markers can be detected with non-denaturing and denaturing electrophoretic systems using alternative labeling and detection strategies. For example, radioactive and silver staining detection methods, and ethidium bromide staining methods are all applicable. The 6–15 STR loci are sorted into 4 to 5 separate mPCR reactions, each containing 2–4 loci. The three loci are selected such that the amplification products run in non-overlapping regions of the gel (i.e., the base pair lengths of the alleles from different loci do not overlap). Alleles from unknown samples are identified with reference to external standards in adjacent lanes (the same cocktails used in the fluorescent detection scheme (FIG. 5) can be employed.

EXAMPLE 9

Species Specificity

The species specificity of amplification of all STR loci can be determined. Primate DNAs, for example human, baboon, chimpanzee, gorilla, and various bacterial and yeast strains are compared. Additionally, Drosphila, common farm animals, common household pets, and common human flora are also examined. There is no difficulty in obtaining the samples since only 10 μg of DNA are needed to perform over 100 studies. The high similarity of sequence between humans and other primates suggests that some of the loci amplify genomes from non-human primates. It is important to document which loci can be amplified from which species for optimal deployment of the method in the forensic arena. Amplification is not seen in non-primates.

EXAMPLE 10

Kits

The kit includes a container having a oligonucleotide primer pair for amplifying short tandem repeats. The kit can also include standards. One kit includes standards and three oligonucleotide primer pairs. In a preferred embodiment the kit includes sufficient oligonucleotide primer pairs needed to perform mPCR for at least 6–10 loci. The kit can further include the reagents, and established protocols for using the kit. These kits provide for efficient and effective transfer and distribution of the method to the forensic community. The oligonucleotides and reaction mixtures in these kits can be stored at −70 C for extended periods of time. This facilitates mass production and quality control of the reagents needed to provide accurate reagents at a reasonable cost.

EXAMPLE 11

Novel STR Sequence

A novel short tandem repeat sequence (SEQ ID. NO. 26) was identified from a lambda clone containing the X chromosome library by screening with a 30 base pair oligonucleotide of the sequence AGAT tandemly repeated. This locus was identified as HUMSTRXI. The sequence flanking the AGAT repeat was amplified and sequenced. Oligonucleotides were designed to amplify the AGAT repeat SEQ ID. NOS. 21 and 22.

The number of AGAT repeats is variable. The exact sequence length was inferred by length polymorphic short tandem repeat sequences with verification of the end sequences. The STR is between approximately base 153 and 203 of SEQ ID. NO. 26. The sense primer is between bases 61 and 84 and corresponds to SEQ ID. NO. 22 and the antisense primer is the reverse complement of the sequence between base 346 and 369 and corresponds to SEQ ID. NO. 21.

EXAMPLE 12

Results and Benefits Expected

The novel methodology of the present invention provides the most powerful technique to date for the characterization of blood and other body fluids. The increase in credible evidence that this assay produces should result in an increase in the conviction rate for such violent crimes as sexual assault and murder. More importantly, many innocent suspects will be categorically cleared of false accusations. Additional applications would result in increased investigative power in the identification of missing persons, abducted children, military personnel, and human remains from natural and physical disasters. The sensitivity of body fluid identification methods would also be increased well beyond current limits. This would provide obvious benefits in the number of cases in which useful evidence was available.

Another significant improvement over the DNA technology currently used is the profound decrease in the amount of time required to provide results and the amount of labor required to produce the results. The time of actual testing for the new methodology is only 10% of the time required for existing DNA profiling techniques. Furthermore, existing technology is of limited investigative use in sexual assaults and homicides, due to the length of time required to obtain results.

The STR DNA profiling assay enables precise allele determination. The analysis of databases for locus stability, population heterogeneity, population allele frequencies, the Mendelian inheritance are greatly simplified. The collection of data from the fluorescent STR profiling assay lends itself to automation, thereby reducing the chance of operator error. Defined discrete allele designations promote generation of a national databank.

The loci developed, the profiling assay methods, and the population studies are of interest to the general scientific community- DNA profiling has direct application in the medical diagnostic and research laboratories for verifying specimen identity.

One skilled in the art will readily appreciate that the present invention is well adapted to carry out the objects and obtain the ends and advantages mentioned, as well as those inherent therein. The oligonucleotides, methods, procedures and techniques described herein are presently representative of the preferred embodiments, are intended to be exemplary, and are not intended as limitations on the scope. Changes therein and other uses will occur to those skilled in the art which are encompassed within the spirit of the invention or defined by the scope of the appended claims.

---

What is claimed is:

1. A DNA profiling assay for detecting polymorphisms in at least one short tandem repeat, comprising the steps of:

extracting DNA from a sample to be tested;
amplifying said at least one short tandem repeat in the extracted DNA, wherein the short tandem repeat sequence is characterized by the formula ($A_wG_x$-

$T_yC_z)_n$ wherein A,G,T, and C represent the nucleotides; w, x, y and z represent the number of each nucleotide and range from 0 to 7; the sum of $w+x+y+z$ ranges from 4 to 7; and n represents the repeat number and ranges from about 5 to 50; and detecting said polymorphisms by identifying said amplified extension products for each different sequence, wherein each different sequence is differentially labelled.

2. The method of claim 1, further comprising an external standard.

3. The method of claim 1, further comprising an internal standard.

4. The method of claim 1, wherein the sample to be tested is a forensic or medical sample selected from the group consisting of blood, semen, vaginal swabs, tissue, hair, saliva, urine, and mixtures of body fluids.

5. The assay of claim 1, wherein at least one short tandem repeat sequence is selected from the non-duplicative alphabetical represented nucleotide sequence group consisting of:

$(AAAC)_n$, $(AAAG)_n$, $(AAAT)_n$, $(AACC)_n$, $(AACG)_n$, $(AAGC)_n$, $(AAGG)_n$, $(AAGT)_n$, $(AATC)_n$, $(AATG)_n$, $(AATT)_n$, $(ACAG)_n$, $(ACAT)_n$, $(AGAT)_n$, $(ACCC)_n$, $(ACCG)_n$, $(ACCT)_n$, $(ACGC)_n$, $(ACGG)_n$, $(ACGT)_n$, $(ACTC)_n$, $(ACTG)_n$, $(AGCC)_n$, $(AGCG)_n$, $(AGCT)_n$, $(AGGC)_n$, $(AGGG)_n$, $(ATCC)_n$, $(ATCG)_n$, $(ATGC)_n$, $(CCCG)_n$, $(CCGG)_n$, and combinations thereof; wherein n is the repeat number and varies from about 5 to 50.

6. The assay of claim 1 wherein n ranges between 5 and 40.

7. The assay of claim 1, wherein n varies from about 5 to 20.

8. The assay of claim 1, wherein the DNA is amplified by PCR or multiplex PCR.

9. The assay of claim 1, wherein amplification is by multiplex PCR with primers to at least two short tandem repeat sequences.

10. The assay of claim 1, wherein the label is selected from the group consisting of fluorescers, radioisotopes, chemiluminescers, stains, enzymes and antibodies.

11. The method of claim 10, wherein the label is fluorescent and is selected from the group consisting of Texas Red, NBD aminoheanoic acid Tetramethylrhodamine-5- (and -6) isothiocyanate, and Fluorescein-5-isothiocyanate.

12. The DNA profiling assay of claim 1, further comprising the step of distinguishing simultaneously differential labels during the detecting step, wherein said labels are distinguished by an automated DNA label analyzer.

13. A kit for a DNA profiling assay to detect polymorphisms in at least one short tandom repeat sequence comprising a container which has oligonucleotide primer pairs for amplifying said at least one short tandem repeat sequence.

14. The kit of claim 13 further comprising a labelled standard.

15. The kit of claim 13 further comprising a container having reagents for multiplex polymerase chain reaction.

16. A method of detecting a polymorphic short tandem repeat comprising the steps of:

determining possible, non-duplicative nucleotide sequences of the formula $(A_wG_xT_yC_z)$, wherein A,G,T and C represents each nucleotide and w,x,y and z represent the number of each nucleotide and ranges between 0 and 7 with the sum of $w+x+y+z$ ranging between 3 and 7;

searching for $(A_wG_xT_yC_z)_n$ in databases containing known genetic sequences, wherein n represents the number of tandem repeats of the genetic sequence and is at least 5;

identifying the $(A_wG_xT_yC_z)_n$ sequence and its flanking sequence;

extracting each identified sequence found in the searching step and its flanking sequence; and identifying the extracted sequences which have unique flanking sequences.

17. The method of claim 16, further comprising the steps of:

synthesizing oligonucleotide primer pairs to the unique flanking sequences;

performing a polymerase chain reaction with the primer pairs on DNA samples from a test population; and detecting polymorphic short tandem repeats in the extension products of the polymerase chain reaction.

18. A method of detecting a polymorphic short tandem repeat comprising the steps of:

synthesizing labelled oligonucleotide probes complementary to said short tandem repeat;

hybridizing the labelled probes to total human λ phage libraries; and sequencing the hybridized plaques.

19. The method of claim 18, wherein the sequencing step, includes the step of subcloning the hybridized plaque.

20. The method of claim 18, wherein the sequencing step, includes the step of direct polymerase chain reaction of the hybridized plaque.

21. The short tandem AGAT repeat as defined in SEQ ID. NO. 26.

22. The assay of claim 8, wherein the primer pairs are selected from the group consisting of SEQ ID. NO. 1 and 2, SEQ ID. NO. 3 and 4, SEQ ID. NO. 5 and 6, SEQ ID. NO. 7 and 8, SEQ ID. NO. 9 and 10, SEQ ID. NO. 11 and 12, SEQ ID. NO. 13 and 14, SEQ ID. NO. 15 and 16, SEQ ID. NO. 17 and 18, SEQ ID. NO. 19 and 20, SEQ ID. NO. 21 and 22, SEQ ID. NO. 5 and 24, SEQ ID. NO. 19 and 25 and Seq. ID NO. 13 and 23.

23. The assay of claim 13, wherein the primer pairs are selected from the group consisting of SEQ ID. o NO. 1 and 2, SEQ ID. NO. 3 and 4, SEQ ID. NO. 5 and 6, SEQ ID. NO. 7 and 8, SEQ ID. NO. 9 and 10, SEQ ID. NO. 11 and 12, SEQ ID. NO. 13 and 14, SEQ ID. NO. 15 and 16, SEQ ID. NO. 17 and 18, SEQ ID. NO. 19 and 20, SEQ ID. NO. 21 and 22, SEQ ID. NO. 5 and 23, SEQ ID. NO. 19 and 24.

24. The sequences of SEQ ID. NO. 1, SEQ ID. NO. 2, SEQ ID. NO. 3, and SEQ ID. NO. 4 for determining flanking sequences of short tandem repeat.

25. The assay of claim 1, wherein the short tandem repeat sequence further includes sequences selected from the non-duplicative alphabetical represented nucleotide sequence group consisting of $(AAC)_n$, $(AAG)_n$, $(AAT)_n$, $(ACC)_n$, $(ACG)_n$, $(ACT)_n$ $(AGC)_n$, $(AGG)_n$, $(ATC)_n$, and $(CCG)_n$.

* * * * *

UNITED STATES PATENT AND TRADEMARK OFFICE
CERTIFICATE OF CORRECTION

PATENT NO. : 5,364,759
DATED : Nov. 15, 1994
INVENTOR(S) : Caskey et al.

Page 1 of 2

It is certified that error appears in the above-indentified patent and that said Letters Patent is hereby corrected as shown below:

Column 3, line 42; insert $(AAGC)_n'$ after "$(AACT)_n$
Column 7, line 22; delete "3-bp." and insert -- 3-5bp. --.
Column 9, lines 31 and 32; move the "-" and the end of line 31 to be beginning of the text on line 32.
Column 9, line 55, delete "$[ATT]_{30}$" and insert -- $[AAT]_{10}$ --.
Column 10, line 40, delete "--DNA" and insert -- -DNA --.
Column 11, line 15, delete "ATp" and insert -- ATP --.
Column 12, line 27, delete "PolymorDhic" and insert -- Polymorphic --.
Column 12, line 40, change the subscript 32 to a superscript 32.
Column 12, line 41, delete "HUM HPRTB" and insert -- HUMHPRTB --.
Column 17, directly under Table 8, footnote a, insert footnotes b, c and d as follows:
  [b]Alleles from all four racial groups were pooled for this column.
  [c]A dash indicates the absence of that allele in the respective sample.
  [d]Refers to the number of chromosomes samples.
Column 17, line 32, delete "0,048" and insert -- 0.048 --.
Column 19, line 64, delete "Red TM" and insert -- Red$^{TM}$ --.
Column 23, delete the first "( 2 )" and insert -- ( 3 ) --.
Column 23, delete the second "( 2 )" and insert -- ( 4 ) --.
Column 23, delete the third "( 2 )" and insert -- ( 5 ) --.
Column 23, delete the fourth "( 2 )" and insert -- ( 6 ) --.
Column 23, delete the fifth "( 2 )" and insert -- ( 7 ) --.
Column 23, delete the sixth "( 2 )" and insert -- ( 8 ) --.
Column 25, delete the first "( 2 )" and insert -- ( 9 ) --.
Column 25, delete the second "( 2 )" and insert -- ( 10 ) --.
Column 25, delete the third "( 2 )" and insert -- ( 11 ) --.
Column 25, delete the fourth "( 2 )" and insert -- ( 12 ) --.
Column 25, delete the fifth "( 2 )" and insert -- ( 13 ) --.
Column 27, delete the first "( 2 )" and insert -- ( 14 ) --.
Column 27, delete the second "( 2 )" and insert -- ( 15 ) --.
Column 27, delete the third "( 2 )" and insert -- ( 16 ) --.
Column 27, delete the fourth "( 2 )" and insert -- ( 17 ) --.
Column 27, delete the fifth "( 2 )" and insert -- ( 18 ) --.

UNITED STATES PATENT AND TRADEMARK OFFICE
CERTIFICATE OF CORRECTION

PATENT NO. : 5,364,759

DATED : Nov. 15, 1994

INVENTOR(S) : Caskey et al.

It is certified that error appears in the above-indentified patent and that said Letters Patent is hereby corrected as shown below:

Column 29, delete the first "( 2 )" and insert -- ( 19 ) --.
Column 29, delete the second "( 2 )" and insert -- ( 20 ) --.
Column 29, delete the third "( 2 )" and insert -- ( 21 ) --.
Column 29, delete the fourth "( 2 )" and insert -- ( 22 ) --.
Column 29, delete the fifth "( 2 )" and insert -- ( 23 ) --.
Column 29, delete the sixth "( 2 )" and insert -- ( 24 ) --.
Column 31, delete the first "( 2 )" and insert -- ( 25 ) --.
Column 31, delete the second "( 2 )" and insert -- ( 26 ) --.
Column 31, delete the third "( 2 )" and insert -- ( 27 ) --.

Column 34, line 51, delete "o" at line end.

Signed and Sealed this

Third Day of October, 1995

Attest:

BRUCE LEHMAN

*Attesting Officer*     *Commissioner of Patents and Trademarks*

US005364759B2

REEXAMINATION CERTIFICATE (3814th)

United States Patent [19]
Caskey et al.

[11] B2 5,364,759
[45] Certificate Issued Jul. 20, 1999

[54] DNA TYPING WITH SHORT TANDEM REPEAT POLYMORPHISMS AND IDENTIFICATION OF POLYMORPHIC SHORT TANDEM REPEATS

[75] Inventors: Charles T. Caskey; Albert O. Edwards, both of Houston, Tex.

[73] Assignee: Baylor College of Medicine, Houston, Tex.

Reexamination Request:
No. 90/004,798, Oct. 14, 1997

Reexamination Certificate for:
Patent No.: 5,364,759
Issued: Nov. 15, 1994
Appl. No.: 07/647,655
Filed: Jan. 31, 1991

Reexamination Certificate B1 5,364,759 issued Nov. 18, 1997

Certificate of Correction issued Oct. 3, 1995.

[51] Int. Cl.$^6$ .............................. C12Q 1/68; C07H 15/12; C07H 21/04; C07H 21/02; G01N 33/48; G01N 33/566; C12P 21/02
[52] U.S. Cl. .......................... 435/6; 435/91.1; 435/91.2; 435/810; 436/94; 536/24.3; 536/24.31; 536/24.33; 536/25.3; 935/77; 935/78
[58] Field of Search .............................. 435/6, 91.2, 810; 536/24.33; 935/77, 78

[56] References Cited

U.S. PATENT DOCUMENTS

| | | | |
|---|---|---|---|
| 4,683,195 | 7/1987 | Mullis et al. | 435/6 |
| 5,075,217 | 12/1991 | Weber | 435/6 |

OTHER PUBLICATIONS

Chamberlain et al., Nuc. Acids Res. 16(23):11141–11156, 1988.
Innis et al., Proc. Natl. Acad. Sci., USA 85:9436–9440, Dec. 1988.
Moyzis et al., Genomics 4:273–289, 1989.
Smith et al., Nature 321:674–679, Jun. 12, 1986.
Smeets, H.J.M. et al., Use of variable simple sequence motifs as genetic markers: Application to study of myotonic dystrophy, 1989, Hum Genet 83:245–251.
Edwards, A. et al., Automated DNA sequencing methods for detection and analysis of mutations: Applications to the Lesch–Nyhan syndrome, 1989, Transaction f the Association of American Physicians CII:185–194.
Williamson, R. et al., Human gene mapping 10.5: 10th International Workshop on Human Gene Mapping, 1990, Cytogenet Cell Genet 55:457–778.
Chehab, F.F. & Kan, Y.W., Detection of specific DNA sequences by fluorescence amplification: A color complementation asay, Dec. 1989, Proc Natl Acad Sci USA 86:9178–9182.
Gibbs, R.A. et al., Diagnosis of new mutation diseases using the polymerase chain reaction, 1989, PCR Technology, New York, pp. 171–191.

Tautz, D.; Trick, M.; & Dover, G.A., Cryptic simplicity in DNA is a major source of genetic variation, Aug. 14, 1986, Nature 322:652–656.
von Beroldingen, C.H., et al., Applications of PCR to the analysis of biological evidence, 1989, PCR Technology, New York, pp. 209–223.
Fowler, J.C.S. et al., Repetitive deoxyribonucleic acid (DNA) and human genome variation—A concise review relevant to forensic biology, Sep. 1988, J. Forensic Sciences 33(5):1111–1126.
Carrano, A.V. et al., A high–resolution, flroescence–based, semiautomated method for DNA fingerprinting, 1989, Genomics 4:129–136.
Jeffreys, A.J.; Wilson, V.; & Thein, S.L., Hypervariable 'minisatellite' regions in human DNA, Mar. 7, 1985, Nature 314:67–73.
Litt, M. & Luty, J.A., A hypervariable microsatellite revealed by in vitro amplification of dinucleotide repeat within the cardiac muscle actin gene, 1989, Am J Hum Genet 44:397–401.
Maniatis, T.; Fritsch, E.F. & Sambrook J. (eds.), Molecular cloning: A laboratory manual, 1982, Cold Spring Harbor Laboratory Press: Cold Spring Harbor, NY.
Nakamura, Y. et al., Variable number of tandem repeat (VNTR) markers for human gene mapping, Mar. 27, 1987, Science 235:1616–1622.
Tautz D., Hypervariability of simple sequences as a general source for polymorphic DNA markers, 1989, Nucleic Acids Research 17(16):6463–6471.
Weber, J.L. & May, P.E., Abundant class of human DNA polymorphisms which can be typed using the polymerase chain reaction, 1989, Am J Hum Genet 44:388–396.

(List continued on next page.)

*Primary Examiner*—Stephanie Zitomer

[57] ABSTRACT

The present invention relates to a DNA profiling assay for detecting polymorphisms in a short tandem repeat. The method includes the steps of extracting DNA from a sample to be tested, amplifying the extracted DNA and identifying the amplified extension products for each different sequence. Each different sequence is differentially labeled. In the method, internal and external standards can also be used. The method is applicable to a wide variety of forensic and medical samples, including blood, semen, vaginal swaps, tissue, hair, saliva, urine and mixtures of body fluids. A short tandem repeat sequence which can be characterized by the formula $(A_wG_{xy}C_z)$, wherein A, G, T and C represent the necleotides, w, x, y and z represent the number of nucleotide and range 0 to 7 and the sum of w+x+y+z ranges from 3 to 7 and n represents the repeat number and ranges from 5 to 50. The labels can be from a variety of groups, including fluorescers, radioisotopes, chemiluminescers, stains, enzymes and antidioisotopes, chemiluminescers, stains, enzymes and antibodies. Also described is a kit. Further, a method of detecting the polymorphic short tandem repeats comprising the steps of either searching for the repeats in a data base or comparing oligonucleotides and searching for the repeats in a genetic library.

OTHER PUBLICATIONS

Schafer, R. Zischler H. & Epplen, J.T., (CAC)5, a very informative oligonucleotide probe for DNA fingerprinting, 1988, Nucleic Acids Res 16(11):5196.

Schafer, R. et al., Optimized oligonucleotide probes for DNA fingerprinting, 1988, Electrophoresis 9:369–374.

Mancuso, D.J. et al., Structure of the gene for human von Willebrand factor, Nov. 25, 1989, J Biol Chem 264(33):19514–19527.

Miklos, G.L.; Matthaei, K.I., & Reed, K.C., Occurrence of the (GATA)n sequences in vertebrate and invertebrate genomes, Sep. 1989, Chromosoma 98(3):194–200.

Devor, E.J & Burgess, A.K., Short synthetic oligonucleotide repeats detect human genomic variation, Aug. 1989, Human Biology 61(4):533–541.

Roberts, R.G. et al. Detection of novel genetic markers by mismatch analysis, Aug. 1989, Nucleic Acids Res 17(15):5961–5971.

Yandell, D.W. & Dryja, T.P., Detection of DNA sequence polymorphisms by enzymatic amplification and direct genomic sequencing, Oct. 1989, Am J Hum Genet 45:547–555.

Smeets, H. et al., Physical and genetic mapping of loci around the myotonic dystrophy (DM) mutation at 19q13, Jun. 1989, Cytogenetics and Cell Genetics 51(1–4):1081 (abstract A2109).

Tautz, D. & Renz M. Simple sequences are ubiquitous repetitive components of eukaryotic genomes, 1984, Nucleic Acids Research 12(10):4127–4138.

Epplen, J.T. et al., Base sequence of a cloned snake W–chromosome DNA fragment and identification of a male–specific putative mRNA in the mouse, Jun. 1982, Proc Natl Acad Sci USA 79:3798–3802.

Gebhar, W. & Zachau, H.G., Simple DNA sequences and dispersed repetitive elements in the vacinity of mouse immunoglobulin K light chain genes, 1983, J Mol Biol 170:567–573.

Weller, P., et al., Organization of the human myoglobin gene, 1984, The EMBO Journal 3(2):439–446.

Goodbourn, S.E.Y. et al., Molecular basis of length polymorphism in the human zeta–globin gene complex, Aug. 1983, Proc Natl Acad Sci USA 80:5022–5026.

Arnemann, J., et al., Clustered GATA repeats (Bkm sequences) on the human Y chromosome, 1986, Hum Genet 73:301–303.

Bell, G.I.; Selby, M.J., & Rutter, W.J., The highly polymophic region near the human insulin gene is composed of simple tandemly repeating sequences, Jan. 7, 1982, Nature 395:31–35.

Sederoff R. & Lowenstein, L., Polyprimidine segments in *Drosophila melanogaster* DNA: II. Chromosome location and nucleotide sequence, 1975, Cell 5:183–194.

Gibbs, R.A. et al., Comprehensive analysis of human HPRT mutations, Oct. 1989, Am J Hum Genet 45(4), Suppl.:abstract 0736.

Boylan, K.B. et al., Repetitive DNA (TGGA)n 5' to the human myelin basic protein gene: A new form of oligonucleotide repetitive sequence showing length polymorphism, Jan. 15, 1990, Genomics 6:16–22.

Fowler, C. et al., Human satellite–III DNA: An example of a "macrosatellite" polymorphism, 1988, Hum Genet 79:265–272.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–12, 16, 17, 21, 22, 24, 25 and 26 is confirmed.

Claims 13 and 18 are determined to be patentable as amended.

Claims 14, 15, 19, 20 and 23, dependent on an amended claim, are determined to be patentable.

13. A kit for a DNA profiling assay to detect polymorphisms in at least one *polymorphic* short tandem repeat sequence, wherein the at least one *polymorphic* short tandem repeat sequence is [characterized] *represented* by the formula $(A_w G_x T_y C_z)_n$, wherein A, G, T, and C represent the nucleotides, w+x+y+z ranges from 3 to 7, and n represents the repeat number and ranges from about 5 to 50, the kit comprising a container which has oligonucleotide primer pairs for amplifying said at least one *polymorphic* short tandem repeat sequence.

18. A method of detecting a polymorphic short tandem repeat sequence, wherein the polymorphic short tandem repeat sequence is [characterized] *represented* by the formula $(A_w G_x T_y C_x)_n$, wherein A, G, T, and C represent the nucleotides, w+x+y+z range from 3 to 7, and n represents the repeat number and ranges from about 5 to 50, the method comprising the steps of:

synthesizing labelled oligonucleotide probes complementary to said polymorphic short tandem repeat;

hybridizing the labelled probes to total human λ phage libraries; and sequencing the hybridized plaques.

* * * * *